(12) United States Patent
Huber

(10) Patent No.: US 9,371,302 B2
(45) Date of Patent: Jun. 21, 2016

(54) LIPIDIC FURAN, PYRROLE, AND THIOPHENE COMPOUNDS FOR TREATMENT OF CANCER

(71) Applicant: Avoscience, LLC, Hayden, ID (US)

(72) Inventor: Richard Huber, Liberty Lake, WA (US)

(73) Assignee: AvoScience, LLC, Hayden, ID (US)

( * ) Notice: Subject to any disclaimer, the term of this patent is extended or adjusted under 35 U.S.C. 154(b) by 0 days.

(21) Appl. No.: 14/229,130

(22) Filed: Mar. 28, 2014

(65) Prior Publication Data

US 2014/0309274 A1   Oct. 16, 2014

Related U.S. Application Data

(60) Provisional application No. 61/853,163, filed on Mar. 29, 2013.

(51) Int. Cl.

| | | |
|---|---|---|
| A61K 31/34 | (2006.01) | |
| A61K 31/38 | (2006.01) | |
| C07D 307/36 | (2006.01) | |
| A61K 31/341 | (2006.01) | |
| A61K 45/06 | (2006.01) | |
| C07D 333/10 | (2006.01) | |
| A61K 31/381 | (2006.01) | |
| C07D 207/32 | (2006.01) | |
| A61K 31/40 | (2006.01) | |
| A61K 31/443 | (2006.01) | |

(52) U.S. Cl.
CPC ............. *C07D 307/36* (2013.01); *A61K 31/341* (2013.01); *A61K 31/381* (2013.01); *A61K 31/40* (2013.01); *A61K 45/06* (2013.01); *C07D 207/32* (2013.01); *C07D 333/10* (2013.01); *A61K 31/443* (2013.01)

(58) Field of Classification Search
CPC .......................... A61K 31/381; A61K 31/443
USPC ................................................. 514/448, 461
See application file for complete search history.

(56) References Cited

U.S. PATENT DOCUMENTS

| | | | | |
|---|---|---|---|---|
| 3,590,028 | A * | 6/1971 | Arcamone | ............. 536/6.4 |
| 4,427,693 | A | 1/1984 | Haber | |
| 5,082,856 | A | 1/1992 | Taniguchi et al. | |
| 5,468,490 | A | 11/1995 | Huber et al. | |
| 5,514,709 | A | 5/1996 | Counts et al. | |
| 6,960,594 | B2 | 11/2005 | Labrecque et al. | |
| 7,037,937 | B2 * | 5/2006 | Uckun | ........ C07D 213/30 514/473 |
| 7,375,105 | B2 | 5/2008 | Dean et al. | |
| 7,589,121 | B2 | 9/2009 | Piccirilli et al. | |
| 2004/0018258 | A1 | 1/2004 | Piccirilli et al. | |
| 2005/0124684 | A1 * | 6/2005 | Du et al. | ............. 514/448 |
| 2008/0081837 | A1 | 4/2008 | Piccirilli et al. | |
| 2008/0219937 | A1 | 9/2008 | Msika et al. | |
| 2013/0183289 | A1 | 7/2013 | Gorelik et al. | |

FOREIGN PATENT DOCUMENTS

| | | |
|---|---|---|
| WO | WO 2007/032591 | 3/2007 |
| WO | WO 2008/080986 | 7/2008 |

OTHER PUBLICATIONS

Buu-Hoi et al., "Thiophene derivatives of potential biological interest. Part IV. Tuberculostatic thiophen compounds" Journal of the Chemical Society, 1953; 547-549.
Cailleau, R. et al., "Long-term human breast carcinoma cell lines of metastatic origin: preliminary characterization" In Vitro, 1978; 11: 911-915.
Hackett et al., "Two syngeneic cell lines from human breast tissue: the aneuploid mammary epithelial (Hs 578T) and the diploid myoepithelial (Hs 578Bst) cell lines" J. Natl. Cancer Inst., 1977; 58(6): 1795-1806.
Kashman, Y. et al., "New Compounds from Avocado Pear" Tetrahedron, 1969; 25: 4617-4631.
Kashman, Y. et al., "Six New C17-olefinic and Acetylenic Oxygenated Compounds from Avocado Pear" Israel Journal of Chemistry, 1969; 7: 173-176.
Laczko et al. "Active lysyl oxidase (LOX) correlates with FAK/paxillin activation and migration in invasive astrocytes" Neuropathol Appl Neurobiol., 2007; 33: 631-643.
Mohamed et al., "Synthesis of mycalazol and mycalazal analogs with potent antiproliferating activities" Pure Appl. Chem., 2011; 83(3): 489-493.
Muller et al. "Single-step induction of mammary adenocarcinoma in transgenic mice bearing the activated c-neu oncogene" Cell, 1988; 54: 105-115.
Neeman, I. et al., "New antibacterial agent isolated from the avocado pear" Appl. Microbiol., 1970; 19: 470-473.
Papireddy, K. et al., "Antimalarial Activity of Natural and Synthetic Prodiginines" J. Med. Chem., 2011; 54: 5296-5306.
Payne et al., "Lysyl oxidase regulates breast cancer cell migration and adhesion through a hydrogen peroxide-mediated mechanism" Cancer Res., 2005; 65: 11429-11436.
PUBCHEM. Compound Summary for CID 8029, Create Date: Sep. 16, 2004. [retrieved on Oct. 15, 2014]. Retrieved from the internet. <URL: https://pubchem.ncbi.nlm.nih.gov/summary/summary.cgi?cid=8029&loc=ec_rcs>.
Rodriguez-Saona C. et al., "Avocadofurans and Their Tetrahydrofuran Analogues: Comparison of Growth Inhibitory and Insecticidal Activity", J. Agric. Food Chem., 2000; 48: 3642-3645.
Rodriguez-Saona C. et al., "Novel Antifeedant and Insecticidal Compounds from Avocado Idioblast Cell Oil" J. Chem. Ecol., 1998, 24: 867-889.
Toxicology and carcinogenesis studies of furan (CAS No. 110-00-9) in F344/N Rats and B6C3F1 mice (gavage studies). National Toxicology Program Technical Report Series No. 402, Jan. 1993. [retrieved on Oct. 15, 2014]. Retrieved from the Internet. <URL: http://ntp.niehs.nih.gov/ntp.htdocs.lt_rpts/tr402.pdf>.

* cited by examiner

*Primary Examiner* — Kevin E Weddington
(74) *Attorney, Agent, or Firm* — Knowles Intellectual Property Strategies; Brent R. Bellows

(57) ABSTRACT

Compounds, methods, and compositions are provided for the treatment of cancer, neurological disorders, and fibrotic disorders. Specifically, the invention includes administering an effective amount of a compound of Formula I, II, or III, or a pharmaceutically acceptable composition, salt, isotopic analog, prodrug, or combination thereof, to a subject suffering from a cancer, neurological disorder, or fibrotic disorder.

21 Claims, 5 Drawing Sheets

LIPIDIC FURAN, PYRROLE, AND THIOPHENE COMPOUNDS FOR TREATMENT OF CANCER

RELATED APPLICATIONS

This application is related to and claims the benefit of provisional U.S. Application No. 61/853,163, filed Mar. 29, 2013. The entirety of this provisional application is hereby incorporated by reference for all purposes.

FIELD OF THE INVENTION

The present invention is directed to compounds, methods, and compositions for the treatment of cancer, neurological disorders, and fibrotic disorders.

BACKGROUND

Every year, cancer claims the lives of more than half a million Americans. Cancer is the second leading cause of death in the United States, exceeded only by heart disease. One of every four deaths in the United States is cancer-related.

Cancers arise from cells that have undergone genetic alterations, leading to abnormal proliferation on a clonal basis. These genetic alterations can include activation of oncogenes or inactivation of tumor suppressors. Different types of cancers have been found to have a wide range of underlying genetic alterations and vary in their pathological progression to the cancerous state, including in their ability to invade surrounding normal tissues and metastasize.

Conventional approaches to cancer treatment include surgery, radiation, and chemotherapy, or a combination thereof. However, for more aggressive and invasive cancers, these treatments have less of an effect than cancers caught at earlier stages of progression. Firstly, invasive cancers appear to be inherently more resistant to a wider variety of chemotherapeutic agents. Secondly, the invasive progression of and metastatic potential of cancer is complex and still poorly understood.

Likewise, neurological disorders such as Parkinson's disease, Alzheimer's disease, or other neurodegenerative disorders that generally start late in life affect nearly one in three seniors. Currently, there are no cures for these types of disorders, and researchers are looking for new treatments to alter the course of the disease and improve the quality of life for those with dementia-like disorders.

Fibrotic diseases, which include pulmonary fibrosis, systemic sclerosis, liver cirrhosis and cardiovascular disease, account for over 45% of deaths in the developed world. In the United States, for example, while some prescribed medications may stabilize subjects who have pulmonary fibrosis, there are currently no FDA-approved therapies, and lung transplantation remains the most viable course of treatment to extend the lives of those with pulmonary fibrosis.

Accordingly, there is a continuing need to identify new treatments to target these devastating disorders.

SUMMARY

Compounds, methods, and compositions are provided for the treatment of cancer, neurological disorders, and fibrotic disorders. Specifically, the invention includes administering an effective amount of a compound of Formula I, II, or III or a pharmaceutically acceptable composition, salt, isotopic analog, prodrug, or combination thereof, to a subject suffering from a cancer, neurological disorder, or fibrotic disorder, wherein Formula I, II or III are:

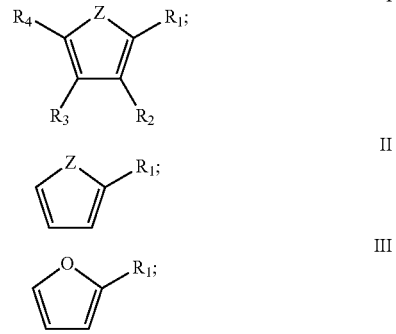

wherein;
each Z is independently O, S or $NR_5$;
wherein $R_1$, $R_2$, $R_3$ and $R_4$, are the same or different, separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$; a $C_1$-$C_{35}$ alkenyl radical, advantageously $C_{10}$-$C_{22}$, more advantageously $C_{12}$-$C_{20}$, further advantageously $C_{13}$-$C_{17}$; or a $C_1$-$C_{35}$ alkynyl radical, advantageously $C_{10}$-$C_{22}$, more advantageously $C_{12}$-$C_{20}$, further advantageously $C_{13}$-$C_{17}$, and wherein the alkyl, alkenyl or alkynyl moiety is optionally substituted with one or more halogens (F, Cl, Br, or I, and more typically F) and/or by one or more moieties selected from the group consisting of epoxide (e.g, an oxygen divalently linked to the carbon chain), hydroxyl or protected hydroxyl ($OR_5$), thiol or protected thiol ($SR_5$), amine ($NR_5R_6$), aldehyde (—CHO), ketone (—$COR_5$), acetyl (—O—CO—$R_5$), or ester (—C(O)$OR_5$) function and wherein $R_5$ and $R_6$ separately represent a hydrogen atom, a $C_1$-$C_{35}$, more typically a $C_1$ to $C_{20}$ alkyl radical, advantageously $C_{10}$-$C_{22}$, more advantageously $C_{12}$-$C_{20}$, further advantageously $C_{13}$-$C_{17}$, or a $C_1$-$C_{35}$ alkenyl radical, advantageously $C_{10}$-$C_{22}$, more advantageously $C_{12}$-$C_{20}$, or further advantageously $C_{13}$-$C_{17}$.

In one embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ saturated carbon chain. In another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain optionally with one, two or three double or triple bonds or a combination thereof. In one embodiment the $R_1$ has one, two or three double bonds, and wherein the two double bonds can be conjugated or non-conjugated and wherein the three double bonds can be fully, partially or non-conjugated. In one embodiment, a double bond can be in the terminal position. In another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain with at least one double and at least one triple bond. In yet another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain with one triple bond. In one embodiment, the triple bond can be in the terminal position.

In one embodiment, $R_1$ is a $C_{11-25}$ saturated carbon chain. In one embodiment, $R_1$ is a $C_{13}$-$C_{17}$ saturated carbon chain. In one embodiment, $R_1$ is a $C_{11}$, $C_{13}$, $C_{15}$, $C_{17}$, $C_{19}$, $C_{21}$, $C_{23}$, or $C_{25}$ saturated carbon chain. In another embodiment, $R_1$ is a $C_{11}$, $C_{13}$, $C_{15}$, $C_{17}$, $C_{19}$, $C_{21}$, $C_{23}$, or $C_{25}$ carbon chain optionally with one, two or three double or triple bonds or a combination thereof. In one embodiment the $R_1$ has one, two or three double bonds, and wherein the two double bonds can be conjugated or non-conjugated and wherein the three double bonds can be fully, partially or non-conjugated. In one embodiment, a double bond can be in the terminal position. In another embodiment, $R_1$ is a $C_{11}, C_{13}, C_{15}, C_{17}, C_{19}, C_{21}, C_{23}$, or $C_{25}$ carbon chain with at least one double and at least one triple bond. In yet another embodiment, $R_1$ is a $C_{11}, C_{13}, C_{15}, C_{17}, C_{19}, C_{21}, C_{23}$, or $C_{25}$ carbon chain with one triple bond. In one embodiment, the triple bond can be in the terminal position.

The double bond can be in the Z or E configuration. In one embodiment, $R_1$ has one or two double bonds in the Z configuration. In an alternative embodiment, one or two double bonds are in the E configuration. For example, when conjugated, the double bonds can be: (2Z, 5Z); (3Z, 6Z), (7Z, 10Z), (8Z, 11Z), (9Z, 12Z), (10Z, 13Z), (11Z, 14Z), or (12Z, 15Z). In an alternative embodiment, $R_1$ has a single double bond in the Z configuration. In one embodiment, the double bond can be (2Z), (3Z), (4Z), (5Z), (6Z), (7Z), (8Z), (9Z), (10Z), (11Z), (12Z), (13Z), (14Z), (15Z), (16Z), (17Z), (18Z), or (19Z). In one embodiment, $R_1$ has a single double bond in the E configuration. In one embodiment, the double bond can be (2E), (3E), (4E), (5E), (6E), (7E), (8E), (9E), (10E), (11E), (12E), (13E), (14E), (15E), (16E), (17E), (18E), or (19E). In one embodiment, the double bonds can be: (2Z, 5E); (3Z, 6E), (7Z, 10E), (8Z, 11E), (9Z, 12E), (10Z, 13E), (11Z, 14E), or (12Z, 15E). In one embodiment, the double bonds can be: (2E, 5Z); (3E, 6Z), (7E, 10Z), (8E, 11Z), (9E, 12Z), (10E, 13Z), (11E, 14Z), or (12E, 15Z).

In one embodiment, $R_1$ is substituted with at least one $OR_5$ group. In one sub-embodiment, $R_1$ is substituted with at least one $OR_5$ group wherein $R_5$=H.

In one embodiment, $R_1$ is substituted with at least two $OR_5$ groups. In one sub-embodiment, $R_1$ is substituted with at least two $OR_5$ group wherein $R_5$=H.

In one embodiment, $R_1$ is substituted with at least three $OR_5$ groups. In one sub-embodiment, $R_1$ is substituted with at least three $OR_5$ group wherein $R_5$=H.

In one embodiment, $R_1$ is substituted with at least one $OR_5$ group. In one sub-embodiment, $R_1$ is substituted with at least one $OR_5$ group wherein $R_5$=C(O)CH$_3$.

In one embodiment, $R_1$ is substituted with at least two $OR_5$ groups. In one sub-embodiment, $R_1$ is substituted with at least two $OR_5$ group wherein $R_5$=C(O)CH$_3$.

In one embodiment, $R_1$ is substituted with at least three $OR_5$ groups. In one sub-embodiment, $R_1$ is substituted with at least three $OR_5$ group wherein $R_5$=C(O)CH$_3$.

In one embodiment, $R_1$ is substituted with at least one $NR_5R_6$ group. In one sub-embodiment, $R_1$ is substituted with at least one $NR_5R_6$ group wherein $R_5$=$R_6$=H.

In one embodiment, $R_1$ is substituted with at least two $NR_5R_6$ groups. In one sub-embodiment, $R_1$ is substituted with at least two $NR_5R_6$ group wherein $R_5$=$R_6$=H.

In one embodiment, $R_1$ is substituted with at least three $NR_5R_6$ groups. In one sub-embodiment, $R_1$ is substituted with at least three $NR_5R_6$ group wherein $R_5$=$R_6$=H.

In one embodiment, $R_1$ is CH$_3$—(CH$_2$)$_m$—(CH=CH)$_x$—(CH$_2$)$_n$ wherein n, m and x do not equal 0 and m+2x+n1 to 35.

In some embodiments, the compound has Formula I:

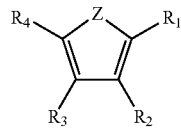

wherein;
Z is independently O, S, NR$_5$;
$R_1$=$R_2$=$R_3$=H;
$R_4$ is a $C_9$-$C_{20}$ alkyl chain comprising two or more double bonds optionally substituted as defined above.

In some embodiments, the compound has Formula II:

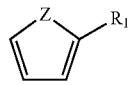

wherein;
$R_1$ is a $C_9$-$C_{20}$ alkyl chain comprising two or more double bonds optionally substituted as defined above.

In some embodiments, the compound has Formula III:

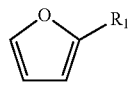

wherein;
$R_1$ is a $C_9$-$C_{20}$ alkyl chain comprising two or more double bonds optionally substituted as defined above.

In an alternative embodiment, the furan, thiophene, or pyrrole can be fused to another heterocyclic or heteroaromatic moiety to produce a multi-ring core, for example, benzofuran, benzothiophene, or indole, which may optionally be substituted with one or more functional groups, preferably with one or more alkyl, alkoxy, halo, or hydroxy substituents.

In one embodiment, a compound of Formula I, Formula II or Formula III has a purity of greater than 95%, greater than 96%, greater than 97%, greater than 98%, or greater than 99%.

In one embodiment provided herein is a method of reducing growth of a solid tumor in a subject, comprising administering an effective amount of a compound of Formula I, II, or III, or a pharmaceutically acceptable composition, salt, isotopic analog, prodrug, or combination thereof. The tumor can be a primary tumor or a metastatic tumor. In one embodiment, a tumor is, for example, a colon tumor, an ovarian tumor, a lung tumor, an esophageal tumor, a breast tumor, a prostate tumor, a carcinoma, or a cancer of the skin. In one embodiment, the compound administered is Formula I(n).

In one embodiment, provided herein is a method for inhibiting the cellular migration of cancer cells in a subject comprising administering an effective amount of a compound of Formula I, II, or III, or a pharmaceutically acceptable composition, salt, isotopic analog, prodrug, or combination thereof. In one embodiment, the compound administered is Formula I(n).

In one embodiment provided herein is a method of treating a skin cancer or pre-cancerous lesion of the skin, comprising administering an effective amount of a compound of Formula I, II, or III, or a pharmaceutically acceptable composition, salt, isotopic analog, prodrug, or combination thereof. In one embodiment, the skin cancer or pre-cancerous lesion of the skin is selected from the group consisting of all pre-cancerous lesions, such as actinic keratosis and leukoplakia, and of all non-melanoma skin cancers such as squamous cell carcinoma and basal cell carcinoma. In one embodiment, the compound administered is Formula I(n).

The compounds described herein can be administered to the subject in combination with other chemotherapeutic agents used for the treatment of cancer or proliferative disorders. If convenient, the compounds described herein can be administered at the same time as another chemotherapeutic agent, in order to simplify the treatment regimen. In some embodiments, the compound and the other chemotherapeutic can be provided in a single formulation. In one embodiment, the use of the compounds described herein is combined in a therapeutic regime with other agents.

Also provided herein is a method of treating a neurological disorder in a subject comprising administering an effective amount of a compound of Formula I, II, or III, or a pharmaceutically acceptable composition, salt, isotopic analog, prodrug, or combination thereof. In one embodiment, the neurological disorder is Alzheimer's disease. In one embodiment, the neurological disorder is Parkinson's disease. In one embodiment, the neurological disease is dementia. In one embodiment, the compound administered is Formula I(n).

In one embodiment provided herein is a method of treating a fibrotic disorder, comprising administering an effective amount of a compound of Formula I, II, or III, or a pharmaceutically acceptable composition, salt, isotopic analog, prodrug, or combination thereof. In one embodiment, the fibrotic disorder is selected from rheumatoid arthritis, surgical adhesions, osteoarthritis, visible skin scars, or a cardiovascular, liver, kidney, lung or periodontal fibrotic disorder, diseases entailing excess collagen and elastin deposition, cutaneous keloid formation, progressive systemic sclerosis, liver cirrhosis, idiopathic and pharmacologically induced pulmonary fibrosis, chronic graft-versus-host disease, scleroderma (local and systemic), Peyronie's disease, pharmacologically induced fibrosis of the penis, post-cystoscopic urethral stenosis, post-surgical internal adhesions, myelofibrosis, and idiopathic and pharmacologically induced retroperitoneal fibrosis. In one embodiment, the fibrotic disorder is rheumatoid arthritis.

In some embodiments, the subject or host is a mammal, including a human. The compound can be administered to the subject by any desired route, including intravenous, sublingual, buccal, oral, intraaortal, topical, intranasal, parenteral, transdermal, systemic, intramuscular, or via inhalation.

In summary, the present invention includes the following features:

A) Compounds of Formula I, II, or III as described herein, and pharmaceutically acceptable compositions, salts, isotopic analogs, or prodrugs thereof, for use in the inhibition of the proliferation of cancer cells in a subject. In one embodiment, the compound is Formula I(n);

B) Compounds of Formula I, II, or III as described herein, and pharmaceutically acceptable compositions, salts, isotopic analogs, or prodrugs thereof, for use in the inhibition of the migration of cancer cells in a subject. In one embodiment, the compound is Formula I(n);

C) A compound as described herein, or a pharmaceutically acceptable composition, salt, isotopic analog, or prodrug thereof, for use as a chemotherapeutic in the treatment of cancer. In one embodiment, the compound is Formula I(n);

D) A compound as described herein, or a pharmaceutically acceptable composition, salt, isotopic analog, or prodrug thereof, for use in combination with a second chemotherapeutic agent in a subject undergoing a therapeutic regime to treat a cancer. In one embodiment, the compound is Formula I(n);

E) Use of a compound described herein, or a pharmaceutically acceptable composition, salt, isotopic analog, or prodrug thereof, in the manufacture of a medicament for use as a chemotherapeutic to treat a subject with a cancer;

F) Processes for the preparation of therapeutic products that contain an effective amount of a compound described herein, for use in the treatment of a subject having a cancer;

G) A method for manufacturing a medicament selected from the compounds described herein intended for therapeutic use as a chemotherapeutic for the treatment of a cancer.

H) Compounds of Formula I, II, or III as described herein, and pharmaceutically acceptable compositions, salts, isotopic analogs, or prodrugs thereof, for use in the treatment of a subject suffering from a neurological disorder. In one embodiment, the compound is Formula I(n);

I) Use of a compound described herein, or a pharmaceutically acceptable composition, salt, isotopic analog, or prodrug thereof, in the manufacture of a medicament for use as a treatment in a subject with a neurological disorder;

J) Processes for the preparation of therapeutic products that contain an effective amount of a compound described herein, for use in the treatment of a subject having a neurological disorder;

K) A method for manufacturing a medicament selected from the compounds described herein intended for therapeutic use as a in the treatment of a neurological disorder;

L) Compounds of Formula I, II, or III as described herein, and pharmaceutically acceptable compositions, salts, isotopic analogs, or prodrugs thereof, for use in the treatment of a subject suffering from a fibrotic disorder. In one embodiment, the compound is Formula I(n);

M) Use of a compound described herein, or a pharmaceutically acceptable composition, salt, isotopic analog, or prodrug thereof, in the manufacture of a medicament for use as a treatment in a subject with a fibrotic disorder;

N) Processes for the preparation of therapeutic products that contain an effective amount of a compound described herein, for use in the treatment of a subject having a fibrotic disorder;

O) A method for manufacturing a medicament selected from the compounds described herein intended for therapeutic use as a in the treatment of a fibrotic disorder.

P) Compounds as described herein for use to treat a solid tumor, neurological disorder, or fibrotic disorder, wherein the active ingredient is not provided as a botanical extract mixture or combination, but instead the active compound is delivered in a highly pure form. In one embodiment, the invention is a dosage form for the treatment of a solid tumor, neurological disorder, or fibrotic disorder, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, II or III as described herein.

DETAILED DESCRIPTION OF THE INVENTION

Figures 1A, 1B:
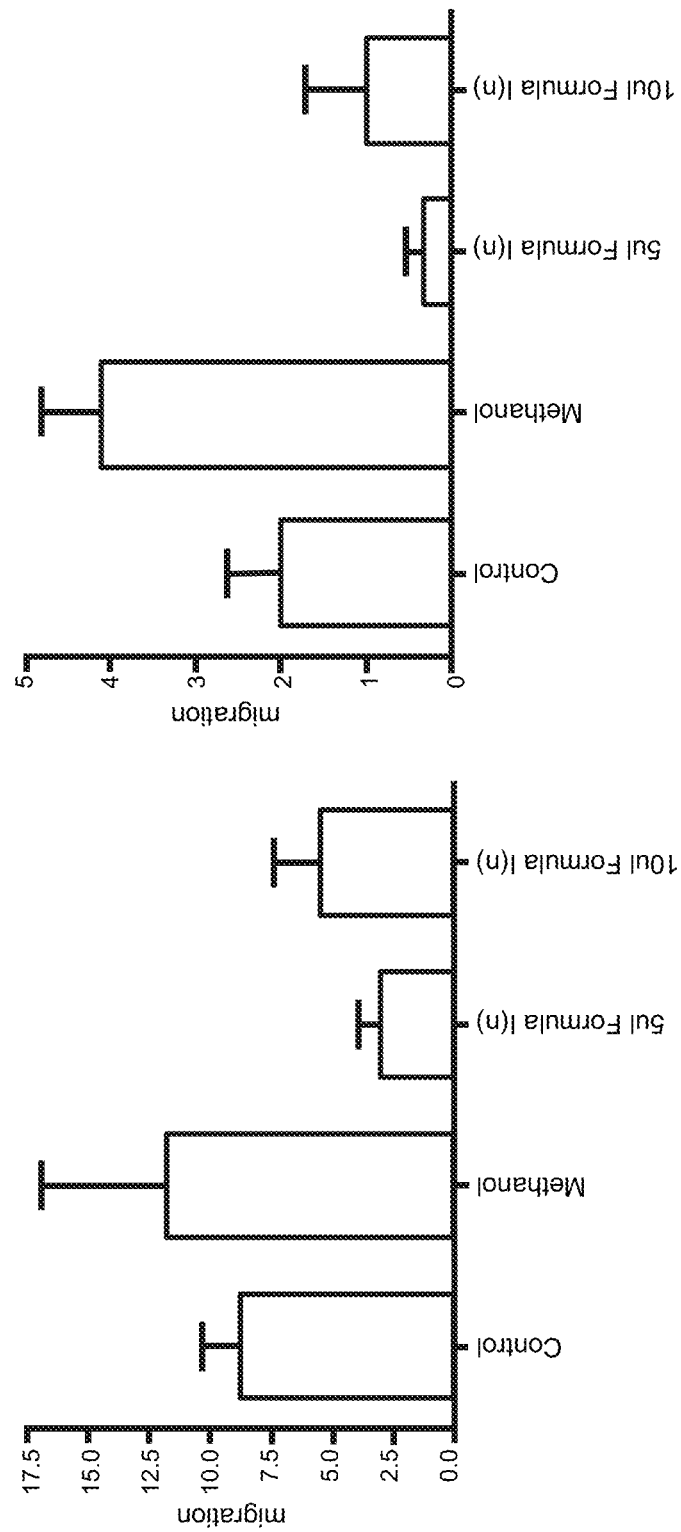
FIG. 1A is graph of cell migration using the breast cancer cell line MDA-MB231 for cells treated with 0 µl/10 ml, 5 µl/10 ml and 10 µl/10 ml Formula I(n). The effect of Formula I(n) on the migration of MDA-MB231 invasive breast tumor cells was tested using the Membrane Invasion Culture System (MICS) chamber. The Membrane Invasion Culture System (MICS) chamber was assembled with Crosstex 10 µm polycarbonate membrane pre-soaked in gelatin for 12 hours. The lower wells were fully loaded with DMEM supplemented with 10% FBS and 0, 5, 10 µl/10 ml Formula I(n) diluted in 0-20 µl/10 ml methanol. The upper wells were loaded with 1 ml serum-free phenol-red-free media and corresponding Formula I(n)/methanol solution. 100,000 cells/well were loaded and the chamber was incubated at 37° C. for 24 hours. After the incubation the media from the upper part of the chamber was removed and non-migratory cells from the upper surface of the membrane were wiped away with Kimwipe. The cells were fixed onto the membrane by immersing it in 100% MeOH. Cells were stained in Eosin solution for 25 seconds and in crystal violet solution for 35 sec. The membrane was rinsed in water, placed onto a microscope slide pre-treated with immersion oil, covered with a coverslip and cells were counted under a light microscope. Each sample was measured in triplicate. As described in Example 6, Formula I(n) significantly inhibited MDA-MB231 tumor cell migration.
FIG. 1B is graph of cell migration using the breast cancer cell line Hs578T for cells treated with 0 µl/10 ml, 5 µl/10 ml and 10 µl/10 ml Formula I(n). The effect of Formula I(n) on the migration of Hs578T invasive breast tumor cells was tested using the Membrane Invasion Culture System (MICS) chamber, using the protocol described in FIG. 1A. As described in Example 6, Formula I(n) significantly inhibited Hs578T tumor cell migration.

The present invention concerns lipidic furan, pyrrole, and thiophene compounds, methods, and compositions for treatment of cancer, neurological disorders, and fibrotic disorders.

DEFINITIONS

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) Advanced Organic Chemistry 5th Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in March's Advanced Organic Chemistry: Reactions, Mechanisms, and Structure, 6th Edition, M. B. Smith and J. March, John Wiley & Sons, Inc., Hoboken, N.J., 2007.

The term "lipidic furan" as used herein refers a compound comprising a furan ring substituted with at least one branched, straight chain or cyclic hydrocarbon group, preferably a linear hydrocarbon chain, more preferably comprising a linear hydrocarbon chain comprising one or more ethylenic or acetylenic unsaturations.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Active Compounds

In one embodiment, the invention is directed to compounds or the use as described herein of such compounds of Formula I, II or III;

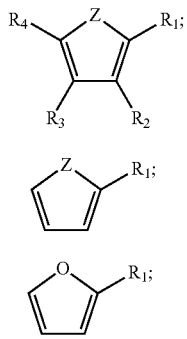

wherein;
each Z is independently O, S or $NR_5$;
wherein $R_1$, $R_2$, $R_3$ and $R_4$, are the same or different, separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$; a $C_1$-$C_{35}$ alkenyl radical, advantageously $C_{10}$-$C_{22}$, more advantageously $C_{12}$-$C_{20}$, further advantageously $C_{13}$-$C_{17}$; or a $C_1$-$C_{35}$ alkynyl radical, advantageously $C_{10}$-$C_{22}$, more advantageously $C_{12}$-$C_{20}$, further advantageously $C_{13}$-$C_{17}$, and wherein the alkyl, alkenyl or alkynyl moiety is optionally substituted with one or more halogens (F, Cl, Br, or I, and more typically F) and/or by one or more moieties selected from the group consisting of epoxide (e.g., an oxygen divalently linked to the carbon chain), hydroxyl or protected hydroxyl ($OR_5$), thiol or protected thiol ($SR_5$), amine ($NR_5R_6$), aldehyde (—CHO), ketone (—$COR_5$), acetyl (—O—CO—$R_5$), or ester (—C(O)$OR_5$) function and wherein $R_5$ and $R_6$ separately represent a hydrogen atom, a $C_1$-$C_{35}$, more typically a $C_1$ to $C_{20}$ alkyl radical, advantageously $C_{10}$-$C_{22}$, more advantageously $C_{12}$-$C_{20}$, further advantageously $C_{13}$-$C_{17}$, or a $C_1$-$C_{35}$ alkenyl radical, advantageously $C_{10}$-$C_{22}$, more advantageously $C_{12}$-$C_{20}$, or further advantageously $C_{13}$-$C_{17}$.

In some embodiments, the compound has Formula I(a):

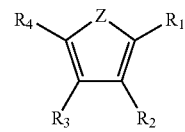

wherein;
Z is independently O, S, $NR_5$;
$R_1$=$R_2$=$R_3$=H;
$R_4$=$C_{13}$-$C_{19}$ alkyl optionally substituted as defined above.

In some embodiments, the compound has Formula I(b):

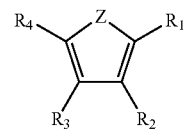

wherein;
Z is independently O, S, $NR_5$;
$R_1$=$R_2$=$R_3$=H;
$R_4$ is a straight $C_9$-$C_{20}$ unsaturated alkyl chain with a single double bond of the formula —CH=CH($CH_2$)$_m CH_3$;
optionally substituted as defined above;
wherein;
m=6 to 17.

In some embodiments, the compound has Formula I(c):

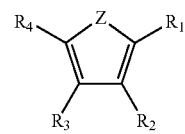

wherein;
Z is independently O, S, $NR_5$;
$R_1$=$R_2$=$R_3$=H;
$R_4$ is a straight $C_{13}$-$C_{19}$ unsaturated alkyl chain with a single double bond of the formula —CH=CH($CH_2$)$_m CH_3$;
optionally substituted as defined above;
wherein;
m=10 to 16.

In some embodiments, the compound has Formula I(d):

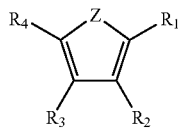

wherein;
Z is independently O, S, NR$_5$;
R$_1$=R$_2$=R$_3$=H;
R$_4$ is a straight C$_9$-C$_{20}$ unsaturated alkyl chain with a single double bond of the formula —(CH$_2$)$_n$—CH=CH(CH$_2$)$_m$CH$_3$;
optionally substituted as defined above;
wherein
n=1 to 17;
m=1 to 17.

In some embodiments, the compound has Formula I(e):

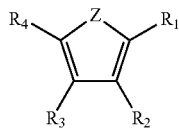

wherein;
Z is independently O, S, NR$_5$;
R$_1$=R$_2$=R$_3$=H;
R$_4$ is a straight C$_{13}$-C$_{19}$ unsaturated alkyl chain with a single double bond of the formula —(CH$_2$)$_n$—CH=CH(CH$_2$)$_m$CH$_3$;
optionally substituted as defined above;
wherein
n=1 to 15;
m=1 to 15.

In some embodiments, the compound has Formula I(f):

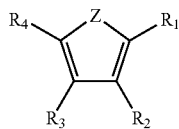

wherein;
Z is independently O, S, NR$_5$;
R$_1$=R$_2$=R$_3$=H;
R$_4$ is a straight C$_9$-C$_{20}$ unsaturated alkyl chain with a single double bond of the formula —(CH$_2$)$_m$CH=CH$_2$;
optionally substituted as defined above;
wherein;
m=7 to 18.

In some embodiments, the compound has Formula I(g):

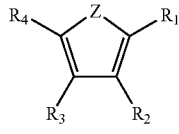

wherein;
Z is independently O, S, NR$_5$;
R$_1$=R$_2$=R$_3$=H;
R$_4$ is a straight C$_{13}$-C$_{19}$ unsaturated alkyl chain with a single double bond of the formula —(CH$_2$)$_m$CH=CH$_2$;
optionally substituted as defined above;
wherein;
m=11 to 17.

In some embodiments, the compound has Formula I(h):

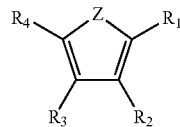

wherein;
Z is independently O, S, NR$_5$;
R$_1$=R$_2$=R$_3$=H;
R$_4$ is a C$_9$-C$_{20}$ alkyl chain comprising two or more double bonds optionally substituted as defined above.

In some embodiments, the compound has Formula I(i):

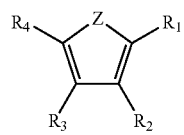

wherein;
Z is independently O, S, NR$_5$;
R$_1$=R$_2$=R$_3$=H;
R$_4$ is a C$_{13}$-C$_{19}$ alkyl chain comprising two or more double bonds optionally substituted as defined above.

In some embodiments, the compound has Formula I(j):

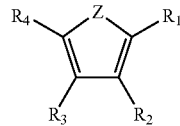

wherein;
Z is independently O, S, NR$_5$;
R$_1$=R$_2$=R$_3$=H;
R$_4$ is a C$_9$-C$_{20}$ alkyl chain comprising one or more triple bonds optionally substituted as defined above.

In some embodiments, the compound has Formula I(k):

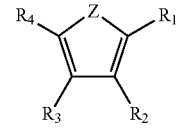

wherein;
Z is independently O, S, NR$_5$;
R$_1$=R$_2$=R$_3$=H;
R$_4$ is a C$_{13}$-C$_{19}$ alkyl chain comprising one or more triple bonds optionally substituted as defined above.

In some embodiments, the compound has Formula I(l):

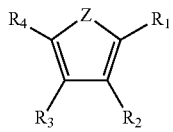

wherein;
Z is independently O, S, NR$_5$;
R$_1$=R$_2$=R$_3$=H;
R$_4$ is a C$_9$-C$_{20}$ alkyl chain comprising one or more double bonds and one or more triple bonds optionally substituted as defined above.

In some embodiments, the compound has Formula I(m):

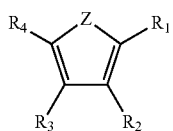

wherein;
Z is independently O, S, NR$_5$;
R$_1$=R$_2$=R$_3$=H;
R$_4$ is a C$_{13}$-C$_{19}$ alkyl chain comprising one or more double bonds and one or more triple bonds optionally substituted as defined above.

In an alternative embodiment, the furan, thiophene or pyrrole can be fused to another heterocyclic or heteroaromatic moiety to produce a multi-ring core, for example, benzofuran, benzothiophene, or indole, which may optionally be substituted with one or more functional groups, preferably with one or more alkyl, alkoxy, halo, or hydroxy substituents.

In one embodiment, the compound has Formula I(n):

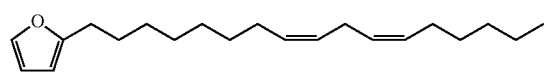 [SMILES: CCCCC/C=C\C/C=C\CCCCCCCc1ccco1]

In one embodiment, the compound has Formula I(o):

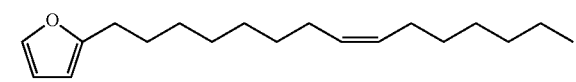 [SMILES: CCCCCC/C=C\CCCCCCCc1ccco1]

In one embodiment, the compound has Formula I(p):

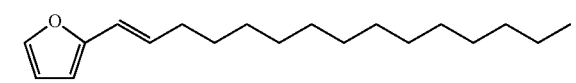 [SMILES: CCCCCCCCCCCCC/C=C/c1ccco1]

In one embodiment, the compound has Formula I(q):

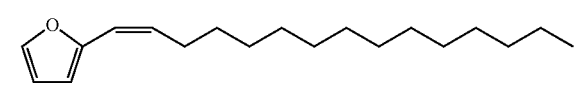 [SMILES: CCCCCCCCCCCCC/C=C\c1ccco1]

In one embodiment, the compound has Formula I(r):

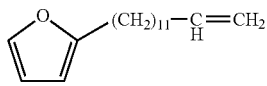

In one embodiment, the compound has Formula I(s):

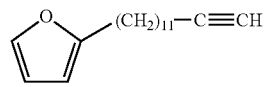

In one embodiment, the compound has Formula I(t):

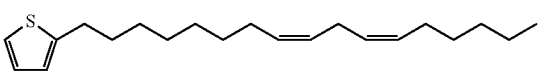

In one embodiment, the compound has Formula I(u):

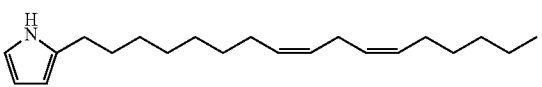 [SMILES: CCCCC/C=C\C/C=C\CCCCCCCc1ccc[nH]1]

In one embodiment, the compound has Formula I(v):

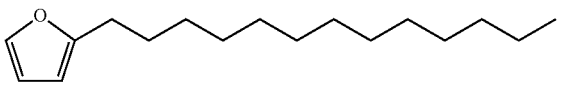

In one embodiment, the compound has Formula I(w):

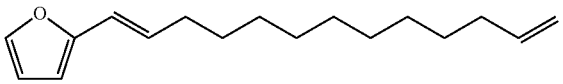

In one embodiment, the compound has Formula I(x):

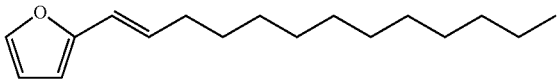

In one embodiment, the compound has Formula I(y):

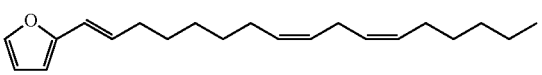

In one embodiment, the compound has Formula I(z):

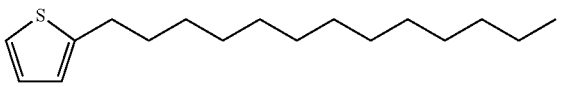 [SMILES: CCCCCCCCCCCCCc1cccs1]

In one embodiment, the compound has the Formula I(aa):

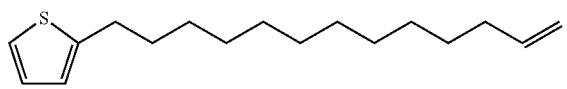 [SMILES: C=CCCCCCCCCCCCc1cccs1]

In one embodiment, the compound has the Formula I(ab):

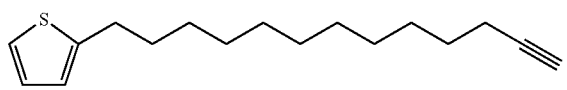 [SMILES: C#CCCCCCCCCCCCc1cccs1]

In one embodiment, the compound has the Formula I(ac):

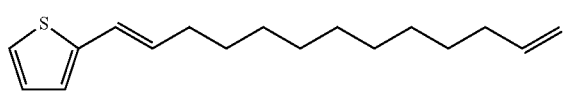 [SMILES: C=CCCCCCCCCC/C=C/c1cccs1]

In one embodiment, the compound has the Formula I(ad):

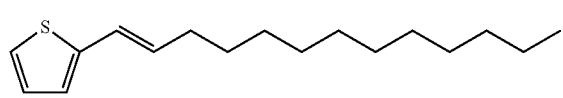

In one embodiment, the compound has the Formula I(ae):

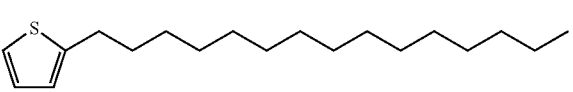 [SMILES: CCCCCCCCCCCCCCCc1cccs1]

In one embodiment, the compound has the Formula I(af):

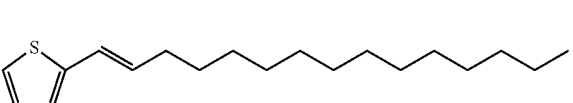

In one embodiment, the compound has the Formula I(ag):

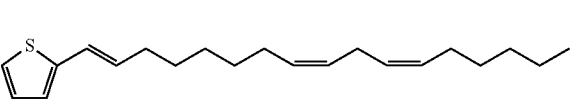 [SMILES: CCCCC/C=C\C/C=C\CCCCC/C=C/c1cccs1]

In one embodiment, the compound has the Formula I(ah):

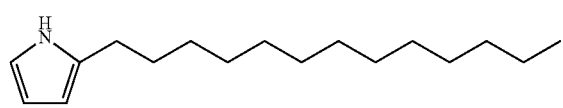 [SMILES: CCCCCCCCCCCCCc1ccc[nH]1]

In one embodiment, the compound has the Formula I(ai):

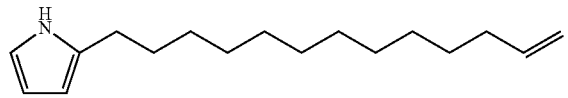 [SMILES: C=CCCCCCCCCCCCc1ccc[nH]1]

In one embodiment, the compound has the Formula I(aj):

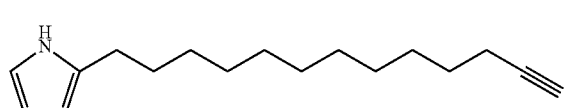

In one embodiment, the compound has the Formula I(ak):

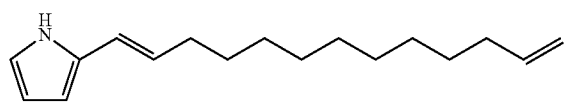 [SMILES: C=CCCCCCCCCC/C=C/c1ccc[nH]1]

In one embodiment, the compound has the Formula I(al):

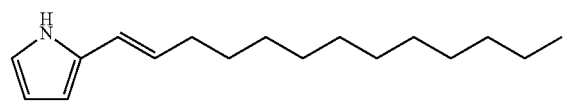 [SMILES: CCCCCCCCCCC/C=C/c1ccc[nH]1]

In one embodiment, the compound has the Formula I(am):

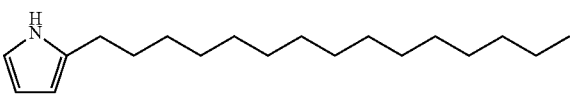 [SMILES: CCCCCCCCCCCCCCCc1ccc[nH]1]

In one embodiment, the compound has the Formula I(an):

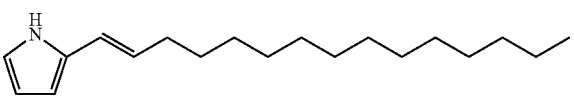 [SMILES: CCCCCCCCCCCCC/C=C/c1ccc[nH]1]

In one embodiment, the compound has the Formula I(ao):

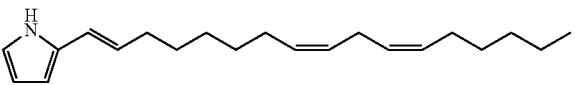 [SMILES: CCCCC/C=C\C/C=C\CCCCC/C=C/c1ccc[nH]1]

In one embodiment the compound of Formula I is 2-(nonanyl)furan.
In one embodiment the compound of Formula I is 2-(dodecyl)furan.
In one embodiment the compound of Formula I is 2-(tridecyl)furan.
In one embodiment the compound of Formula I is 2-(tetradecyl)furan.
In one embodiment the compound of Formula I is 2-(pentadecyl)furan,
In one embodiment the compound of Formula I is 2-(hexadecyl)furan, In one embodiment the compound of Formula I is 2-(heptadecyl)furan In one embodiment the compound of Formula I is 2-(octadecyl)furan).

In one embodiment the compound of Formula I is 2-(nonadecyl)furan).

In one embodiment the compound of Formula I is 2-(8Z-pentadecenyl)furan.

In one embodiment the compound of Formula I is 2-(1E-pentadecenyl)furan.

In one embodiment the compound of Formula I is 2-(1Z-pentadecenyl)furan.

In one embodiment the compound of Formula I is 2-(12-tridecenyl)furan.

In one embodiment the compound of Formula I is 2-(8Z,11Z-heptadecadienyl)furan.

In one embodiment the compound of Formula I is 2-(8Z,11Z-heptadecadienyl)thiophene.

In one embodiment the compound of Formula I is 2-(8Z,11Z-heptadecadienyl)pyrrole.

In one embodiment the compound of Formula I is lignoceric furan.

In one embodiment the compound of Formula I is lauroleic furan.

In one embodiment the compound of Formula I is palmitoleic furan.

In one embodiment the compound of Formula I is cis-vaccenic furan.

In one embodiment the compound of Formula I is erucic furan.

In one embodiment the compound of Formula I is nervonic furan.

In one embodiment the compound of Formula I is arachidonic furan.

In one embodiment the compound of Formula I is crepenynic furan.

Certain furan, pyrrolo, and thiophene derivatives have been of interest in the petroleum, electronic and pharmaceutical industries for certain disorders. Notwithstanding this research, it has now been surprisingly discovered that the presently disclosed active compounds can be advantageously used to treat solid tumors. Thus this invention can be used to treat cancers including but not limited to solid tumors such as breast, colon, lung, bladder, kidney, liver or pancreatic cancer. It has also not been known to use the presently disclosed active compounds to treat serious neurological disorders such as Alzheimer's, Parkinson's, or dementia, nor fibrotic disorders.

In regard to furan derivatives, Kashman et al. first reported the avocadofurans as a new class of phytochemicals. See, Kashman, Y, et al., "New Compounds from Avocado Pear", Tetrahedron, 25:4617-4631 (1969) and Kashman, Y, et al., "Six New C17-olefinic and Acetylenic Oxygenated Compounds from Avocado Pear", Isr. J. Chem., 7:173-176. The authors isolated 2-(trideca-12-ynyl)furan and 2-(trideca-12-enyl)furan from *P. americana* fruit and seeds. Magalhaes et al. subsequently identified several other 2-alkylfurans with $C_{13}$ mono- and diunsaturated side chains from methanol extracts of avocado seeds [*Persea gratissima* Gartn. (syn. *P. americana*)] from Brazil. See, Magalhaes et al., "The avocatins—a new class of natural products", An. Acd. Bras. Cienc. 42(suppl):45-48 (1970).

Neeman et al. tested a group of eight long-chain aliphatic compounds from avocados for activity against 13 species of bacteria and a yeast and reported that 2-(trideca-12-enyl)furan inhibited growth of *Bacillus subtilis* (Ehrenberg) Cohn and *Staphylococcus aureus* Rosenbach. See, Neeman, I, et al., "New antibacterial agent isolated from the avocado pear", Appl. Microbiol., 19:470-473, (1970). Murakoshi et al. tested 2-(8Z,11Z-heptadecadienyl)furan produced by acid-catalyzed dehydration of persin from avocado leaves against silkworm larvae, *B. mori*, and found no activity at concentrations in the diet up to 300 μg/g. See, Murakoshi et al., J. Appl. Entomol. Zool. 20:87-91 (1976). Rodriguez-Saona, C., et al., disclosed that avocadofurans are active as antifeedants. See, Rodriguez-Saona, C., et al., "Novel Antifeedant and Insecticidal Compounds from Avocado Idioblast Cell Oil", J. Chem. Ecol., 24:867-889 (1998). In addition, the authors disclosed the synthesis of $C_{15}$ and $C_{17}$ 2-(alkyl)furans. The compounds were synthesized by coupling the appropriate bromoalkane with 2-lithiofuran in THF. 2-(1E-pentadecenyl)furan and its Z isomer were prepared by Wittig reaction of the glide prepared from tetradecyl triphenylphosphonium bromide with furfural to accord a 7:3 mixture of Z and E isomers.

The compound 2-(8Z,11Z-heptadecadienyl)furan was synthesized as follows. Linoleic acid was converted to the tetrabromide using bromine in diethyl ether. The carboxylic acid was next decarboxylated and converted to an alkyl bromide using a modified Hunsdiecker reaction. Regeneration of the diene moiety with zinc powder in THF yielded a bromo diene that was converted to the corresponding alkyl iodide and subsequently coupled with 2-lithiofuran to afford the doubly unsaturated avacadofuran.

U.S. Pat. No. 5,468,490 to Huber, S. R. and Counts, D. F. discloses the lipidic furan, 17-(2-furanyl-8-11-cis-cis-heptadecadiene, also referred to as 2-(8Z,11Z-heptadecadienyl) furan), with beneficial effects on the epidermis and dermis of the skin. U.S. Pat. No. 5,514,709 to Counts, D. F. and Huber, R. discloses lipid furans, 2-alkyl furans, and their specificity to types I and III collagen, both of which are present in large amounts in the skin and mucosal tissues. Rodriguez-Saona, C. et al. discloses the synthesis of 2-(pentadecyl)furan and 2-(heptadecyl)furan. See, Rodriquez-Saona, C., et al., "Avocadofurans and Their Tetrahydrofuran Analogues: Comparison of Growth Inhibitory and Insecticidal Activity", J. Agric. Food Chem., 48:3642-3645 (2000). U.S. Pat. Application No. 2004/0018258 to Piccirilli, A. and Legrand, J. discloses the process for obtaining a furan lipid-rich unsaponifiable material from avocado. U.S. Pat. Application No. 2008/0219937 to Msika, P. and Piccardi, N. discloses the use of a cosmetic composition with depigmenting or lightening action comprising as active at least one2-alkyl furan. U.S. Pat. Application No. 2008/0081837 to Piccirilli, A., et al., disclose a method for preventing and/or treating diabetes using 2-alkyl furans wherein the 2-position is substituted with a $C_1$-$C_{35}$ alkyl, $C_1$-$C_{35}$ alkenyl, or $C_1$-$C_{35}$ alkynyl substituent. U.S. Pat. No. 7,589,121 to Piccirilli, A. et al., discloses the use of alkyl furans for the treatment of obesity and obesity. U.S. Pat. Application No. 2013/0183289 to Gorelik, L. et al discloses the use avocadanofuran for the treatment of a DNA virus.

In regard to pyrroles, U.S. Pat. No. 5,082,856 to Taniguchi, M. et al discloses pyrrolecarboxylic acid derivatives for the treatment of hyperlipemia and arteriosclerosis. The authors disclose the synthesis of 2,5-disubstituted, and 2,4-disubstited pyrroles. For example, in Method 1 of the '856 patent, pyrrole is reacted with a methyl or ethyl magnesium halide and the magnesium salt is reacted with an acyl chloride to afford a 2-acylpyrrole. The ketone is subjected to Wolff-Kishner reduction conditions to afford the 2-alkylpyrrole. The 2-alkylpyrrole is then treated with a Grignard reagent followed by ethyl chlorocarbonate to afford 5-alkylpyrrole-2-carboxylate. The ester can be converted to the corresponding carboxylic acid by hydrolyzing the ester under standard conditions. In Method 2 of the '856 patent, ethyl pyrrole-3- carboxylate is reacted with an acyl chloride in the presence of a Lewis acid to obtain the 5-acylpyrrole-3-carboxylate. The resulting ketone is then subjected to Wolff-Kishner reduction conditions to afford an ethyl 5-alkylpyrrole-3-carboxylate. The ester can then be converted to the corresponding carboxylic acid by hydrolyzing the ester under standard conditions.

Mycalazol and mycalazal analogs having antiproliferating activity been disclosed by Mohamed, Y. M. A. and Hansen, T. V. See, Mohamed, Y. M. A. and Hansen, T. V., "Synthesis of mycalazol and mycalazal analogs with potent antiproliferating activities", Pure Appl. Chem., 83(3):489-493 (2011). Using pyrrole 2-carboxaldehyde as the starting material, the authors treated the aldehyde with dimethylamine to form an azafulvene in quantitative yield. The compound was treated with n-butyllithium and excess n-tributyltin chloride to produce 5-(tri-n-butylstannyl)pyrrole-2-carboxaldehyde. Acid chlorides underwent Stille cross-coupling reactions with the stannyl pyrrole to afford 2,5-disubstituted pyrroles.

Papireddy, K. et al. have recently disclosed the antimalarial activity of prodiginines. In this paper, the authors disclosed the synthesis of 2-alkylated pyrroles and 3-alkylated pyrroles. The intermediates were subsequently used to generate synthetic analogs of prodiginines. In order to generate 2-alkylated pyrroles, pyrrole was acylated using zinc powder to afford 2-acylpyrroles. The 2-acylpyrroles were reduced to the corresponding 2-alkylated pyrroles using an excess of sodium borohydride in 2-propanol under reflux. In order to generate 3-alkylated pyrroles, pyrrole was treated with phenylsulfonyl chloride in the presence of sodium hydroxide to provide N-phenylsulfonylpyrrole. Use of aluminum trichloride permitted the regioselective acylation of the N-phenylsulfonylpyrrole at the 3 position with an acyl chloride to afford N-phenylsulfonyl-3-acylpyrroles. The N-phenylsulfonyl-3-acylpyrroles were hydrolyzed under basic conditions to afford 3-acylpyrroles. In the final step, 3-acylpyrroles were reduced to afford 3-alkylpyrroles using sodium borohydride under reflux. See, Papireddy, K. et al., "Antimalarial Activity of Natural and Synthetic Prodiginines", J. Med. Chem., 54:5296-5306 (2011).

In regard to thiophene derivatives, 2,5-disubstituted thiophene analogs were disclosed by Buu-Hoi, N. P, et al. as potential tuberculostatic compounds. See, Buu-Hoi, N. P, et al., Isotopic Substitution The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location.

Therapeutic Treatment of Cancers

Compounds, methods, and compositions are provided to treat a cancer. Improved compounds, methods, and compositions are provided for inhibiting cellular migration of cancer cells. Improved compounds, methods, and compositions are provided that inhibit invasive cancers. Improved compounds, methods, and compositions are provided for inhibiting abnormal cellular proliferation. In one embodiment, the cancer is a solid tumor. In one embodiment, the solid tumor is a non-skin tumor.

In one embodiment of the invention, a compound for the treatment of cancer is selected from the compounds of Formula I, II or III as described herein, or a pharmaceutically acceptable composition, salt, isotopic analog, or prodrug thereof. In one non-limiting example, the cancer is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

According to this invention, the active ingredient is not provided as a botanical extract mixture or combination, but instead the active compound is delivered in a highly pure form. In one embodiment, the invention is a dosage form for the treatment of a solid tumor, which is a non-skin derived tumor or disorder, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, II or III as described herein. In a further alternative embodiment, the dosage form has two or more active ingredients selected from compounds of Formula I, II or III as described herein, wherein each active compound has a purity of at least 96%, 97%, 98%, or 99%, without respect to fillers, stabilizers, or other inert or inactive ingredients.

Further provided herein is a method of reducing growth of a solid tumor in a subject, comprising administering the active compounds described herein. A tumor can be a primary tumor or a metastatic tumor. In one aspect, a solid tumor is, for example, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, or melanoma. In one embodiment, a solid tumor is, for example, a colon tumor, an ovarian tumor, a lung tumor, an esophageal tumor, a breast tumor, a prostate tumor, a carcinoma. In one embodiment of the invention, the cancer is treated with a compound selected from the compounds of Formula I, II or III as described herein, or a pharmaceutically acceptable composition, salt, isotopic analog, or prodrug thereof. In one non-limiting example, the cancer is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

In one embodiment, the cancer is an invasive breast cancer. Invasive breast cancer has spread from the original site (either the milk ducts or lobules) into the surrounding breast tissue, and possibly spread to the lymph nodes and/or other parts of the body. Thus, invasive breast cancers have a poorer prognosis than ductal carcinoma in situ (DCIS), which is a non-invasive breast cancer. Using a microscope to look at the tissue removed during a biopsy, a pathologist can determine whether a tumor is DCIS or invasive breast cancer through analysis of biopsies. The most common type is invasive ductal carcinoma (also called infiltrating ductal carcinoma and less commonly, invasive carcinoma of no special type or invasive carcinoma not otherwise specified). Invasive ductal carcinoma accounts for 50 to 75 percent of all breast cancers. Invasive lobular carcinoma is the next most common type and accounts for about 10 to 15 percent of cases. Tubular carcinoma and mucinous (colloid) carcinoma are less common types of invasive breast cancer that tend to have a good prognosis. In one embodiment of the invention, the breast cancer is treated with a compound selected from the compounds of Formula I, II or III as described herein, or a pharmaceutically acceptable composition, salt, isotopic analog, or prodrug thereof. In one non-limiting example, the breast cancer is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

In one embodiment provided herein is a method of treating a skin cancer comprising administering the active compounds described herein. In one embodiment, the skin cancer is selected from the group consisting of all non-melanoma skin cancers such as squamous cell carcinoma and basal cell carcinoma. In one embodiment, the skin cancer is a melanoma. In one embodiment of the invention, the skin cancer is treated with a compound selected from the compounds of Formula I, II or III as described herein, or a pharmaceutically acceptable composition, salt, isotopic analog, or prodrug thereof. In one non-limiting example, the skin cancer is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

In certain aspects, compounds, methods, and composition are provided for use as chemotherapeutics for treating and/or preventing cancer cell or pre-cancerous lesion expansion, proliferation, o activation, in a patient in need thereof, comprising administering a pharmaceutically effective amount of the compounds described herein. In certain embodiments, compounds, methods, and composition are provided for use as chemotherapeutics for treating and/or preventing cancer cell metastasis or invasion in a patient in need thereof, comprising administering a pharmaceutically effective amount of the compounds described herein. In certain embodiments, compounds, methods, and composition are provided for use as chemotherapeutics for treating and/or preventing cancer cell migration in a patient in need thereof, comprising administering a pharmaceutically effective amount of the compounds described herein. In certain embodiments, compounds, methods, and composition are provided for use as chemotherapeutics for treating and/or preventing cytoskeletal reorganization of the cancer cell in a patient in need thereof, comprising administering a pharmaceutically effective amount of the compounds described herein.

In one embodiment of the invention, a compound(s) of Formula I, having a purity of greater than 98%, is incorporated with an excipient(s) for topical application as a medicament to treat cancerous lesions of the skin. In one embodiment, the amount of the compound of Formula I for topical application ranges from about 0.1% to about 100%. In one embodiment, the amount of the compound of Formula I for topical application ranges from about 1% to about 10%. In another embodiment, the amount of the compound of Formula I for topical application ranges from about 1% to about 5%. In one embodiment of the invention, the excipient is an oil of natural or synthetic origin. In one embodiment, the cancers of the skin include, but are not limited to, non-melanoma skin cancers, squamous cell carcinoma and basal cell carcinoma.

Therapeutic Treatment of Pre-cancerous Lesions

Actinic keratoses (AKs) are common skin lesions heralding an increased risk of developing squamous cell carcinoma (SCC) and other skin malignancies, arising principally due to excessive ultraviolet (UV) exposure. They are predominantly found in fair-skinned individuals, and increasingly, are a problem of the immunosuppressed. Actinic keratoses (AKs) may regress spontaneously, remain stable or transform to invasive SCC.

In one embodiment provided herein is a method of treating and/or preventing a pre-cancerous lesion of the skin, comprising administering the active compounds described herein. In one embodiment, the pre-cancerous lesion of the skin is selected from the group consisting of all pre-cancerous lesions, such as actinic keratoses and leukoplakia. In one embodiment of the invention, a compound for the treatment of a pre-cancerous lesion of the skin is selected from the compounds of Formula I, II or III as described herein, or a pharmaceutically acceptable composition, salt, isotopic analog, or prodrug thereof. In one non-limiting example, the pre-cancerous lesion of the skin is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

According to this invention, the active ingredient is not provided as a botanical extract mixture or combination, but instead the active compound is delivered in a highly pure form. In one embodiment, the invention is a dosage form for the treatment of a precancerous lesion, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, II or III as described herein. In a further alternative embodiment, the dosage form has two or more active ingredients selected from compounds of Formula I, II or III as described herein, wherein each active compound has a purity of at least 96%, 97%, 98%, or 99%, without respect to fillers, stabilizers, or other inert or inactive ingredients.

In one embodiment of the invention, a compound(s) of Formula I, having a purity of greater than 98%, is incorporated with an excipient(s) for topical application as a medicament to treat pre-cancerous lesions of the skin. In one embodiment, the amount of the compound of Formula I for topical application ranges from about 0.1% to about 100%. In one embodiment, the amount of the compound of Formula I for topical application ranges from about 1% to about 10%. In another embodiment, the amount of the compound of Formula I for topical application ranges from about 1% to about 5%. In one embodiment of the invention, the excipient is an oil of natural or synthetic origin. In one embodiment the pre-cancerous lesions of the skin include, but are not limited to, actinic keratosis and leukoplakia. In one embodiment, the pre-cancerous lesion is leukoplakia.

Cancer Combination Therapy

In one aspect of the invention, the compounds disclosed herein can be beneficially administered in combination with another therapeutic regimen for beneficial, additive, or synergistic effect.

In one embodiment, a compound/method of the present invention is used in combination with another therapy to treat cancer. In some embodiments, the compound can be administered to the subject in combination with other chemotherapeutic agents. If convenient, the compounds described herein can be administered at the same time as another chemotherapeutic agent, in order to simplify the treatment regimen. In some embodiments, the compound and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopototic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

In one embodiment, a compound described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™), Vincristine (Oncovin®) or liposomal vincristine (Margibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, vinorelbine tartrate, bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, and celecoxib.

In certain embodiments, a compound described herein is administered to the subject prior to treatment with another chemotherapeutic agent, during treatment with another chemotherapeutic agent, after administration of another chemotherapeutic agent, or a combination thereof.

In one aspect of the invention, a compound disclosed herein can be beneficially administered in combination with any therapeutic regimen entailing radiotherapy, chemotherapy, or other therapeutic agents.

Neurological Disorders

Additional therapeutic uses of the compounds disclosed herein include use in the treatment and/or prevention of neurological disorders. These range from dementia disorders, such as Alzheimer's and Parkinson's where cellular structure deformation is a common denominator; to diseases of the eye such as exfoliating glaucoma. In one embodiment provided herein is a method of treating a neurological disorder, comprising administering an effective amount of a compound described herein. In one embodiment, the neurological disorder is Alzheimer's disease. In one embodiment, the neurological disorder is Parkinson's disease. In one embodiment, the neurological disorder is amyotrophic lateral sclerosis. In one embodiment, the neurological disorder is central or peripheral nervous system damage, dysfunction, or complications stemming from edema, injury, or trauma. In one embodiment, the neurological disorder is Multiple Sclerosis, Alzheimer's disease, Amyotrophic Lateral Sclerosis, Parkinson's disease, Huntington's disease, neuropathic pain, or spinal cord injury. In one embodiment of the invention, a compound for the treatment of the neurological disorder is selected from the compounds of Formula I, II or III as described herein, or a pharmaceutically acceptable composition, salt, isotopic analog, or prodrug thereof. In one non-limiting example, the neurological disorder is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

According to this invention, the active ingredient is not provided as a botanical extract mixture or combination, but instead the active compound is delivered in a highly pure form. In one embodiment, the invention is a dosage form for the treatment of a neurologic disorder such as Alzheimer's, Parkinson's, and dementia, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, II or III as described herein. In a further alternative embodiment, the dosage form has two or more active ingredients selected from compounds of Formula I, II or III as described herein, wherein each active compound has a purity of at least 96%, 97%, 98%, or 99%, without respect to fillers, stabilizers, or other inert or inactive ingredients. In a further alternative embodiment, the dosage form has two or more active ingredients selected from compounds of Formula I, II or III as described herein, wherein each active compound has a purity of at least 96%, 97%, 98%, or 99%, without respect to fillers, stabilizers, or other inert or inactive ingredients.

Neurological Disorder Combination Therapies

In one aspect of the invention, the compounds disclosed herein can be beneficially administered in combination with one or more additional therapeutics for beneficial, additive or synergistic effect to treat a neurological disorder. Therapeutic combinations can include the use of a compound as described herein with a therapeutic used to treat a neurological disorder. Therapies used for the treatment of neurological disorders include, but are not limited to, Abstral, Aggrenox, Aggrenox, Ampyra, Amrix, Anexsia, Apokyn, Aptiom, ARICEPT, Avinza, Avonex, Axert, Axona, Banzel, Botox, Bromfenac, Butrans, Cambia, Carbaglu, Carbatrol, Cenestin, Clalis, Clonazepam, Comtan, Copaxone, Cuvposa, Cylert, Depakote, Durezol, Edluar, Eliquis, Embeda, Exalgo, Exelon, Exparel, Extavia, Fetzima, Focalin, Frova, Fycompa, Galzin, Gralise, Hetlioz, Horizant, Imitrex, Intermezzo, Intuniv, Invega, Iontocaine, Kadian, Kapvay, Levetiracetam, Lamictal, Lazanda, Levitra, Lidoderm Patch, Lunesta, Lupron Depot, Lusedra, Lyrica, Maxalt, Metadate CD, Migranal, Mirapex, Myobloc, Naltrexone HCl, Namenda, Neupro, Neurontin, NORCO tablets, Northera, Novantrone, Nucynta, Nuedexta, Nuvigil, Nymalize, Onfi, Onsolis, Oxecta, Oxtellar XR, Oxycodone and Aspirin, Poicor, Potiga, Pramipexole, Quadramet, Quillivant XR, Qutenza, Rebif, Redux, Relpax, Reminyl, Requip, Rilutek, Rozerem, Sabril, Selegiline, Silenor, Sonata, Sprix, Stavzor, Strattera, Subsys, Tasmar, Tegretol, Tivorbex, Topamax, Trileptal, Trokendi XR, Tysabri, Ultracet, UltraJect, VERSED, Viibryd, Vimpat, Vivitrol, Vpriv, Vyvanse, Xenazine, Xifaxan, Xyrem, Zanaflex, Zipsor, Zohydro ER, Zomig, Zonegran, and Zubsolv.

Fibrotic Disorders

In one embodiment provided herein is a method of treating and/or preventing a fibrotic disorder, comprising administering an effective amount of a compound described herein.

In one embodiment, the fibrotic disorder is a surgical adhesion, osteoarthritis, or a visible skin scar, and rheumatoid arthritis. In one embodiment provided herein is a method of treating a cardiovascular fibrotic disorder such as atherosclerosis or arteriosclerosis, liver fibrotic disorders, kidney fibrotic disorders, lung fibrotic disorders or periodontal fibrotic disorders, comprising administering to a subject in need thereof a compound described herein. In additional embodiments, the compounds provided herein can be used to treat and/or prevent diseases entailing excess collagen and elastin deposition. In a further embodiment, the fibrotic disorder is selected from the group consisting of cutaneous keloid formation, progressive systemic sclerosis, liver cirrhosis, idiopathic and pharmacologically induced pulmonary fibrosis, chronic graft-versus-host disease, scleroderma (local and systemic), Peyronie's disease, pharmacologically induced fibrosis of the penis, post-cystoscopic urethral stenosis, post-surgical internal adhesions, myelofibrosis, and idiopathic and pharmacologically induced retroperitoneal fibrosis. In one embodiment of the invention, a compound for the treatment of a fibrotic disorder is selected from the compounds of Formula I, II or III as described herein, or a pharmaceutically acceptable composition, salt, isotopic analog, or prodrug thereof. In one non-limiting example, the fibrotic disorder is treated with Formula I(a), Formula I(b), Formula I(c), Formula I(d), Formula I(e), Formula I(f), Formula I(g), Formula I(h), Formula I(i), Formula I(j), Formula I(k), Formula I(l), Formula I(m), Formula I(n), Formula I(o), Formula I(p), Formula I(q), Formula I(r), Formula I(s), Formula I(t), Formula I(u), Formula I(v), Formula I(w), Formula I(x), Formula I(y), Formula I(z), Formula I(aa), Formula I(ab), Formula I(ac), Formula I(ad), Formula I(ae), Formula I(af), Formula I(ag), Formula I(ah), Formula I(ai), Formula I(aj), Formula I(ak), Formula I(al), Formula I(am), Formula I(an), or Formula I(ao) as described herein, or a pharmaceutically acceptable composition, salt, isotopic analog, or prodrug thereof.

According to this invention, the active ingredient is not provided as a botanical extract mixture or combination, but instead the active compound is delivered in a highly pure form. In one embodiment, the invention is a dosage form for the treatment of a fibrotic disorder, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, II or III as described herein. In a further alternative embodiment, the dosage form has two or more active ingredients selected from compounds of Formula I, II or III as described herein, wherein each active compound has a purity of at least 96%, 97%, 98%, or 99%, without respect to fillers, stabilizers, or other inert or inactive ingredients.

Fibrotic Combination Therapies

In one aspect of the invention, the compounds disclosed herein can be beneficially administered in combination with one or more therapeutics used to treat fibrotic disorders in order to provide beneficial, additive or synergistic effect. Therapies used for the treatment of fibrotic disorders include, but are not limited to, corticosteroids such as prednisone, cyclophosamide (Cytoxan®), azathioprine (Imuran®), N-Acetylcysteine (NAC), and pirfenidone (Esbriet®, Pirfenex®, Pirespa®).

Pharmaceutical Compositions and Dosage Forms

In one aspect, the invention provides a pharmaceutical composition comprising a pharmaceutically effective amount of the compounds of the present invention and a pharmaceutically acceptable carrier.

The compounds provided herein are administered for medical therapy in a therapeutically effective amount. The amount of the compounds administered will typically be determined by a physician, in the light of the relevant circumstances, including the condition to be treated, the chosen route of administration, the compound administered, the age, weight, and response of the individual patient, the severity of the patient's symptoms, and the like.

The pharmaceutical compositions provided herein can be administered by a variety of routes including oral, parenteral, topical, rectal, subcutaneous, intravenous, intramuscular, and intranasal with a pharmaceutical carrier suitable for such administration. In one embodiment, the compounds are administered in a controlled release formulation.

The compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (as a nonlimiting example, from about 0.1 to about 50% by weight or preferably from about 1 to about 40% by weight) with the remainder being various vehicles or carriers and processing aids helpful for forming the desired dosing form. In one embodiment, the compound is present from about 1% to about 10% by weight.

The compositions for topical administration can take the form of an emulsion, a cream, a lotion, a solution, an anhydrous stick, a serum, etc. The compositions can include from about 0.1% to about 50% by weight of the compound(s) of Formula I. In one embodiment the composition can include from about 0.1% to about 10% by weight of the compound(s) of Formula I.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

The above-described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The present invention also includes pharmaceutically acceptable acid addition salts of compounds of the invention. The acids which are used to prepare the pharmaceutically acceptable salts are those which form non-toxic acid addition salts, i.e. salts containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

Synthesis

Preparation of Active Compounds:

The disclosed compounds can be made by the following general schemes.

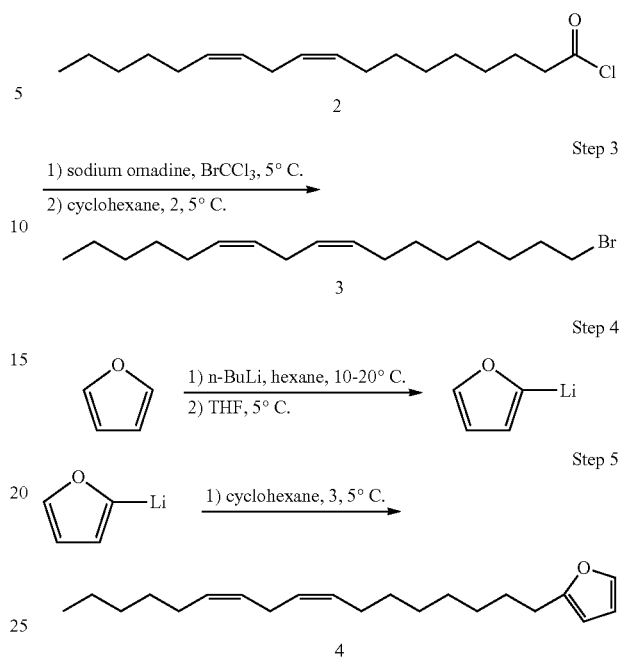

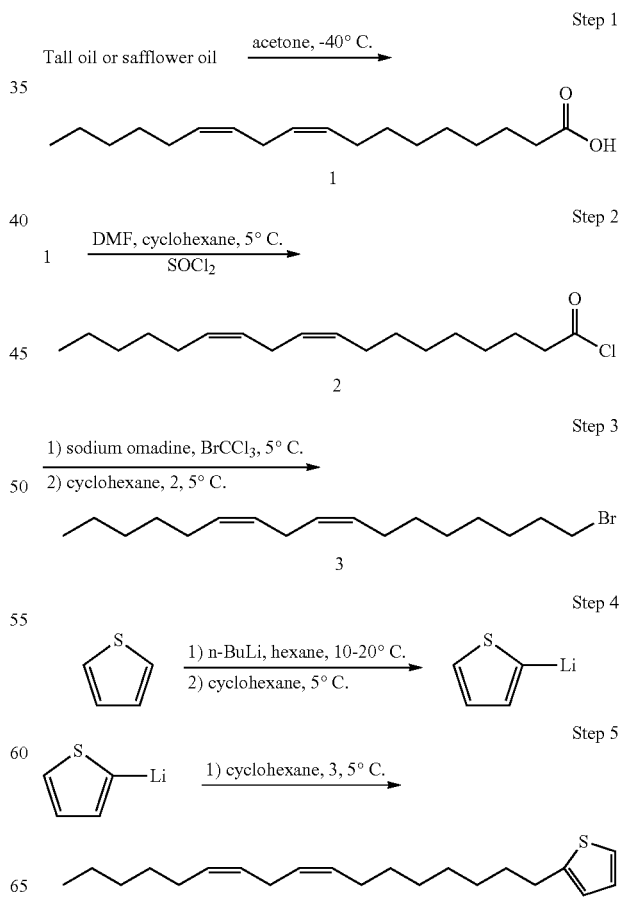

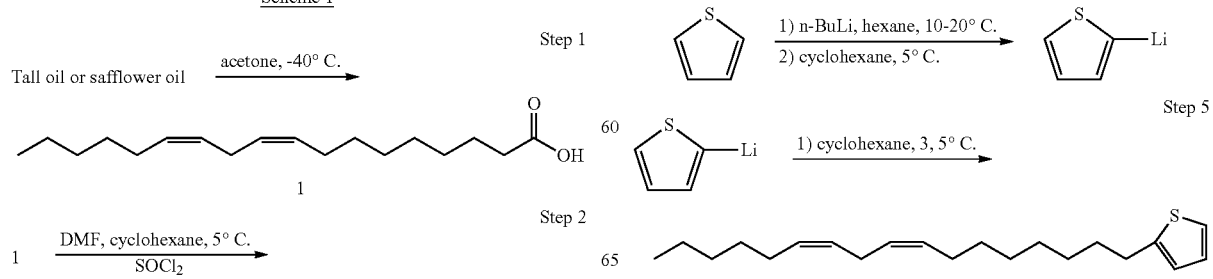

Scheme 3

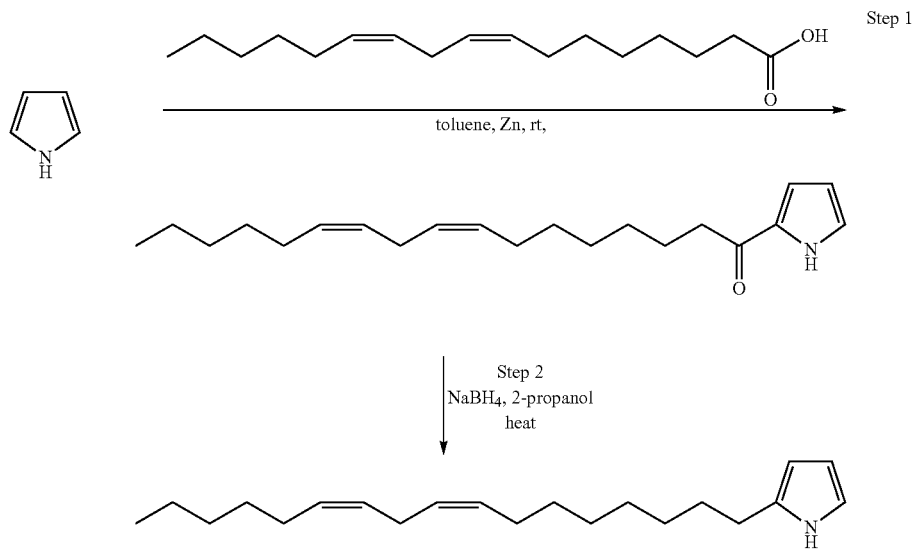

In Scheme 1, Step 1, tall oil or safflower oil is crystallized from an organic solvent such as acetone at reduced temperature to generate linoleic acid. In Step 2, linoleic acid is directly reacted with thionyl chloride in a combination of organic solvents such as dimethylformamide and cyclohexane at reduced temperature to generate an acid chloride. In Step 3, sodium omadine is directly reacted with bromotrichloromethane. The resulting complex is directly reacted with the acid chloride from Step 2 to generate a bromodiene. In Step 4, lithiated furan is generated by directly reacting furan with n-butyllithium. In Step 5, lithiated n-butyllithium is directly reacted with the bromide from Step 3 to generate a furan derivative.

In Scheme 2, Step 4, lithiated thiophene is produced by directly reacting thiophene with n-butyllithium. In Step 5, lithiated thiophene is directly reacted with the bromide of Step 3, Scheme 1 to produce a thiophene derivative.

In Scheme 3, pyrrole is directly reacted with an acid in the presence of zinc powder to generate a ketone. In Step 2, the ketone is directly reacted with a reducing agent such as sodium borohydride in a protic solvent such as 2-propanol to generate a pyrrole derivative.

In another embodiment, compounds of Formula I can be prepared by directly reacting furan or thiophene with an acid chloride using Friedel Craft conditions. The resulting ketone can be reduced with a reducing agent such as sodium borohydride in a protic solvent such as 2-propanol. Alternatively, the ketone can be directly reacted with ethanethiol to generate a thioketal. The thioketal can be reduced using Raney nickel.

In another embodiment, compounds of Formula I can be prepared by directly reacting furaldehyde or thiophenaldehyde with a Wittig reagent to generate an alkene derivative.

In another embodiment, 2-(tri-n-butylstannyl)pyrrole and an acid chloride can be directly reacted using Stille coupling conditions, See, Mohamed, Y. M. A. and Hansen, T. V., Synthesis of mycalazol and mycalazal analogs with potent antiproliferating activities, Purr. Appl. Chem., 83:489-493, 2011. The resulting ketone can be reduced to the corresponding alkane by directly reacting the ketone with palladium on carbon under a hydrogen atmosphere in a protic solvent such as ethanol and an acid catalyst such as sulfuric acid.

EXAMPLES

Example 1

Synthesis of 2-(8Z,11Z-heptadecadienyl)furan (Scheme 1)

Step 1. Preparation of High Purity Linoleic Acid
A1) Obtain conjugated ("c") and preferentially non-conjugated ("nc") linoleic acid (C18) sourced from natural grapeseed (60% nc-10% c) or safflower (60% nc-10% c).
B) Mix vegetable oil with purified water 2:1 to which has been added 0.5% wt/wt of candida rugosa enzymes (Amano 12K) or use an immobilized enzyme bed and recirculate the water and oil mixture. In both examples maintain temperature at not more than 40° C. and not less than 35° C. under a nitrogen blanket. If enzymes are freely mixed then hold at mixing that allows complete recirculation of container contents every 60 seconds and continue for 24 hours. Discontinue reaction and add heptane or other non-polar solvent to solution (approx 0.5:1 ratio), stir and decant under nitrogen and low light. Repeat three times to obtain the fatty acids. Evaporate solvent under nitrogen.
A2) Alternately and preferentially obtain Tall Oil fatty acids that are predominately linoleic (75%) distributed as 90% non-conjugated and 10% conjugated.
C) Mix the fatty acids obtained in B or in A2 and mix with acetone in a ratio of 1 part fatty acid to 3 parts acetone (weight:weight) and bring to −40° C. from 1 to 6 hours and hold for 48 hours at −40° C.
D) Vacuum filter using nominal 5-15 micron filter while chilled at less than −35° C. Evaporate solvent to recover very high purity linoleic acid (>95%).
E) Recover 99% pure linoleic acid (non-conjugated) with flash chromatography or critical fluids chromatography using standard separation protocols.
Step 2. Preparation of Linoleoyl Chloride
A) Add 5 parts DMF (dimethylformamide) to 12,000 parts chilled (5° C.) cyclohexane and 3000 parts chilled (5° C.) linoleic acid and stir under a nitrogen flow of 0.2-0.4 L/min in an ice bath.

B) Add chilled (5° C.) thionyl chloride, SOCl$_2$, dropwise at 3 to 4 mL/min.
C) After all of the thionyl chloride is added, allow the ice bath to come to room temperature and continue stirring under nitrogen flow for 24 hours or until all gas evolution has ceased.
D) Decant cyclohexane from tar layer and evaporate under nitrogen to recover clear amber liquid. Store well sealed in glass containers. The product is obtained in a 90% yield.
Step 3. Preparation of Bromodiene
A) Mix C$_5$H$_5$NOS (sodium omadine) and BrCCl$_3$ (bromotrichlormethane) together in a glass vessel and place at 5° C. for 24 hours to induce crystal formation.
B) Add mixture from Step A to chilled, 5° C., cyclohexane in ice bath and begin nitrogen flow of 0.1-0.3 L/min.
C) Add dropwise chilled, 5° C., linoleoyl chloride from step 2) at not more than 3-4 ml/min to reactor mixture in Step B.
D) After all linoleoyl chloride from step 2 has been added, continue stirring under nitrogen flow. Allow ice bath to melt.
E) Note color change to yellow/red to indicate formation of bromodiene.
F) Follow with decanting and recovery of bromodiene using flash chromatography. The product was isolated in a 50% yield.
Step 4: Preparation Lithiated Furan
1) Prepare a 1M solution of butyllithium in hexane. Note: do not chill below 10° C. to prevent congealing.
2) Add chilled, 5° C., furan to chilled, 5° C., THF.
3) Maintain ice bath.
4) Add butyllithium in hexane dropwise at approximately 3-4 ml/min to chilled furan/THF solution.
5) Maintain ice bath and stir for not longer than 2 hours after all butyllithium has been added. The lithiated furan is obtained in a 90% yield.
Step 5: Synthesis of 2-(8Z,11Z-heptadecadienyl)furan
1. Add approximately 1 part cyclohexane and 1 part bromodiene from Step 3 together and chill to 5° C. and begin nitrogen flow at approximately 0.1 to 0.4 L per minute. Maintain temperature and stir.
2. Add chilled, 5° C., lithiated furan from Step 4 dropwise at approximately 3-4 ml/min. Maintain temperature and stirring.
3. Note color change to dark reddish brown. After all lithiated furan has been added maintain chilled reaction, nitrogen flow and stirring for one hour.
4. After one hour allow temperature to rise to ambient temperature and then maintain stirring and nitrogen for 12 hours.
5. Wash product three times with 3% saline solution mixed with isopropanol or ethanol (1:1) and decant, evaporate solvent.
6. Purify with chromatography.

Example 2

Synthesis of 2-(8Z,11Z-heptadecadienyl)thiophene (Scheme 2)

Steps 1-3 are carried out as described in Example 1.
Step 4: Synthesis of Lithiated Thiophene:
1) Prepare a 1M solution of butyllithium in hexane. Note: do not chill below 10° C. to prevent congealing.
2) Add chilled, 5° C., thiopene to chilled, 5° C., cyclohexane.
3) Maintain ice bath.
4) Add butyllithium in hexane dropwise at approximately 3-4 ml/min to chilled thiopene/cyclohexane solution.
5) Maintain ice bath and stir for not longer than 2 hours after all butyllithium has been added.
6) Work up in standard manner to obtain product.

Step 5: Synthesis of 2-(8Z,11Z-heptadecadienyl)thiophene
1. Add approximately 1 part cyclohexane and 1 part bromodiene from Step 3 together and chill to 5° C. and begin nitrogen flow at approximately 0.1 to 0.4 L per minute. Maintain temperature and stir.
2. Add chilled, 5° C., lithiated thiophene from Step 4 dropwise at approximately 3-4 ml/min. Maintain temperature and stirring.
3. After all lithiated thiopene has been added maintain chilled reaction, nitrogen flow and stirring for one hour.
4. After one hour allow temperature to rise to ambient temperature and then maintain stirring and nitrogen for 12 hours.
5. Wash product three times with 3% saline solution mixed with isopropanol or ethanol (1:1) and decant, evaporate solvent.
6. Purify with chromatography. The product was obtained in a 85% yield.

Example 3

Synthesis of 2-(8Z,11Z-heptadecadienyl)pyrrole (Scheme 3)

Step 1: A mixture of pyrrole (2.0 g, 29.8 mmol) 8Z,11Z-hexadeadienoic acid (17.83 g, 44.7 mmol) and zinc powder (3.88 g, 59.7 mmol) in toluene (75 ml) is stirred at room temperature until the pyrrole is no longer detectable by thin layer chromatography or HPLC. The reaction is quenched with saturated sodium bicarbonate solution (50 ml) and extracted with ethyl acetate (3×30 ml). The combined organic layers are washed with water, dried over anhydrous Na$_2$SO$_4$, filtered and concentrated in vacuo. The product is purified by using silica gel column chromatography that is eluted with a dichloromethane-methanol gradient.
Step 2:
To a stirred solution of the ketone from step 1 (1.63 g, 5.18 mmol), in 150 ml of 2-propanol at ambient temperature is slowly added sodium borohydride (1.34 g, 36.26 mmol). The reaction is heated at reflux and monitored by thin layer chromatography or HPLC. Once the starting material is no longer detected, the reaction is poured into 150 ml of ice-water and the solution is acidified with 10% aqueous HCl. The reaction is extracted with dichloromethane (3×50 ml). The combined organic extracts are washed with water, brine, and dried over anhydrous Na$_2$SO$_4$, filtered and concentrated in vacuo. The product is purified by using silica gel column chromatography that is eluted with a dichloromethane-methanol gradient.

Example 4

2-(8Z,11Z-Heptadecadienyl)furan formulation

According to one embodiment of the present invention,

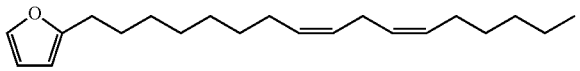

2-(8Z,11Z-heptadecadienyl)furan

A formulation is prepared comprising 2-(8Z,11Z-heptadecadienyl)furan having a purity of greater than 98% and a compound of Formula I having a purity of greater than 98% in a ratio of 80 parts to 20 parts. The two components are added to a vegetable oil base and encapsulated for human oral consumption. The total amount of 2-(8Z,11Z-heptadecadienyl)furan and a compound of Formula I as expressed as a percent of the finished product can vary from 0.1 to 100%, with a preferred amount at about 5%. The vegetable oil carrier may be selected from any commonly produced for human consumption.

Example 5

Lipidic Furan Formulation

According to another embodiment of the invention,

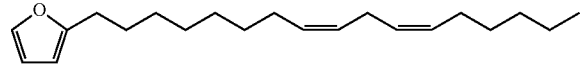

2-(8Z,11Z-heptadecadienyl)furan

The lipidic furan, 2-(8Z,11Z-heptadecadienyl)furan, can be incorporated in a vegetable oil base for orally dosed pharmaceutical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 5% for better dietary uptake and absorption in a vehicle of vegetable oil ordinarily provided for human consumption.

Example 6

Formula I(n) Inhibits Invasive Tumor Cell Migration

The effect of Formula I(n) on the migration of MDA-MB231 and Hs578T invasive breast tumor cells was tested using the Membrane Invasion Culture System (MICS) chamber. MDA-MB231 cells are breast adenocarcinoma cells and are available from ATCC (Cailleau R, et al. Long-term human breast carcinoma cell lines of metastatic origin: preliminary characterization. In Vitro 14: 911-915, 1978). Hs578T cells are breast carcinoma cells and are available from ATCC (Hackett A J, et al. Two syngeneic cell lines from human breast tissue: the aneuploid mammary epithelial (Hs 578T) and the diploid myoepithelial (Hs 578Bst) cell lines. J. Natl. Cancer Inst. 58: 1795-1806, 1977).

The Membrane Invasion Culture System (MICS) chamber was assembled with Crosstex 10 µm polycarbonate membrane pre-soaked in gelatin for 12 hours. The lower wells were fully loaded with DMEM supplemented with 10% FBS and 0, 5, 10 µl/10 ml Formula I(n) diluted in 0-20 µl/10 ml methanol. The upper wells were loaded with 1 ml serum-free phenol-red-free media and corresponding Formula I(n)/methanol solution. 100,000 cells/well were loaded and the chamber was incubated at 37° C. for 24 hours. After the incubation, the media from the upper part of the chamber was removed and non-migratory cells from the upper surface of the membrane were wiped away with Kimwipe. The cells were fixed onto the membrane by immersing it in 100% MeOH. Cells were stained in Eosin solution for 25 seconds and in crystal violet solution for 35 seconds. The membrane was rinsed in water, placed onto a microscope slide pretreated with immersion oil, covered with a coverslip and cells were counted under a light microscope. Each sample was measured in triplicate.

As shown in FIG. 1, cells were treated with 5 µl or 10 µl/10 ml Formula I(n) and evaluated compared to untreated control cells and control cells exposed to the same concentration of methanol used as a solvent for Formula I(n) (10 µl/10 ml). As shown in FIG. 1, Formula I(n) significantly inhibited tumor cell migration in both MDA-MB231 and Hs578T breast cancer cell lines.

Example 7

Formula I(n) Promotes a Stable Mesenchymal Cell Phenotype

Tumor cell behavior is affected to a great degree by the phenotype of the surrounding stromal cells and interactions between the epithelial and mesenchymal cell types. To determine if Formula I(n) also affects mesenchymal cells, migratory ability of fibroblasts in the presence of Formula I(n) was tested.

Figure 2A:
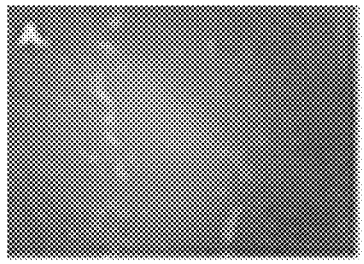
FIG. 2A is a micrograph of an in vitro scratch assay using fibroblasts showing the migration of fibroblasts at 0 hours without treatment of Formula I(n). Confluent cultures of foreskin fibroblasts (Clonetics) were scratched with the tip of a 200 µl pipet tip, rinsed once with PBS and media was changed to serum free media containing 0 µl/10 ml Formula I(n). Pictures were taken at the indicated time (0, 12, or 24 hours) following scratching and the distance between the migrating lips were measured in pixels.
Figure 2B:
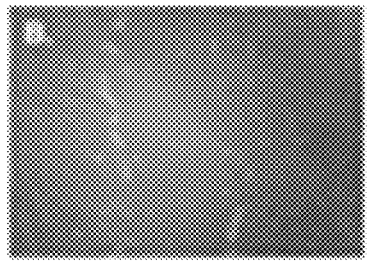
FIG. 2B is a micrograph of an in vitro scratch assay using fibroblasts showing the migration of fibroblasts at 0 hours upon treatment with 5 µl/10 ml Formula I(n). Experiments were conducted as described in FIG. 2A, using 5 µl/10 ml Formula I(n).
Figure 2C:
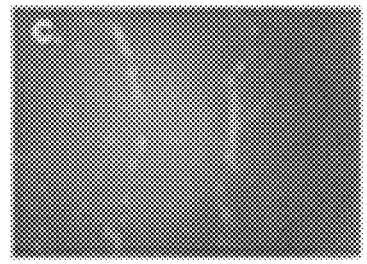
FIG. 2C is a micrograph of an in vitro scratch assay using fibroblasts showing the migration of fibroblasts at 0 hours upon treatment with 10 µl/10 ml Formula I(n). Experiments were conducted as described in FIG. 2A, using 10 µl/10 ml Formula I(n).
Figure 2D:
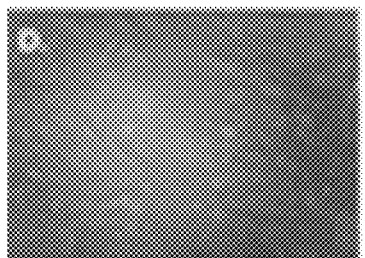
FIG. 2D is a micrograph of an in vitro scratch assay using fibroblasts showing the migration of fibroblasts at 12 hours without treatment of Formula I(n). Experiments were conducted as described in FIG. 2A.
Figure 2E:
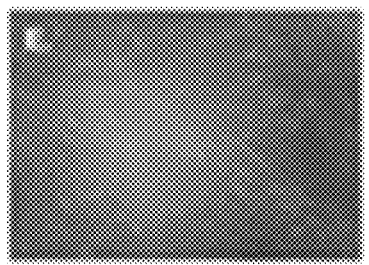
FIG. 2E is a micrograph of an in vitro scratch assay using fibroblasts showing the migration of fibroblasts at 12 hours upon treatment with 5 µl/10 ml Formula I(n). Experiments were conducted as described in FIG. 2A, using 5 µl/10 ml Formula I(n). As described in Example 7, Formula I(n) treated cells showed reduced migration.
Figure 2F:
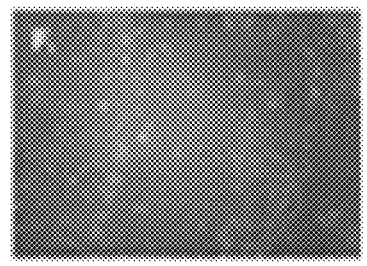
FIG. 2F is a micrograph of an in vitro scratch assay using fibroblasts showing the migration of fibroblasts at 12 hours upon treatment with 10 µl/10 ml Formula I(n). Experiments were conducted as described in FIG. 2A, using 10 µl/10 ml Formula I(n). As described in Example 7, Formula I(n) treated cells showed reduced migration.

Confluent cultures of foreskin fibroblasts (Clonetics) were scratched with the tip of a 200 µl pipet tip, rinsed once with PBS and media was changed to serum free media containing 0 (FIGS. 2A, 2D, 2G) 5 (FIGS. 2B, 2E, 2H) or 10 (FIGS. 2C, 2F) µl/10 ml Formula I(n). Pictures were taken at 0 (FIGS. 2A, 2B, 2C), 12 (FIG. 2D, 2E, 2F) or 24 (FIGS. 2G, 2H) hours following scratching and the distance between the migrating lips were measured in pixels. FIG. 3 is a graph of the distance between the migrating lips (as measured in pixels) vs. the time (hours) after administration of Formula I(n).

Figure 2G:
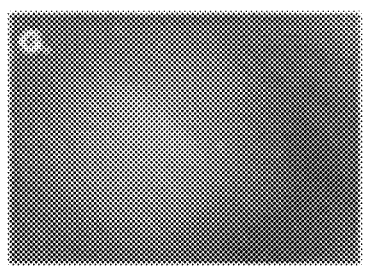
FIG. 2G is a micrograph of an in vitro scratch assay using fibroblasts showing the migration of fibroblasts at 24 hours without treatment of Formula I(n). Experiments were conducted as described in FIG. 2A.
Figure 2H:
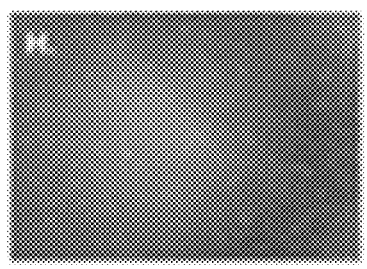
FIG. 2H is a micrograph of an in vitro scratch assay using fibroblasts showing the migration of fibroblasts at 24 hours upon treatment with 5 µl/10 ml Formula I(n). Experiments were conducted as described in FIG. 2A, using 5 µl/10 ml Formula I(n). As described in Example 7, Formula I(n) treated cells showed reduced migration.
Figure 3:
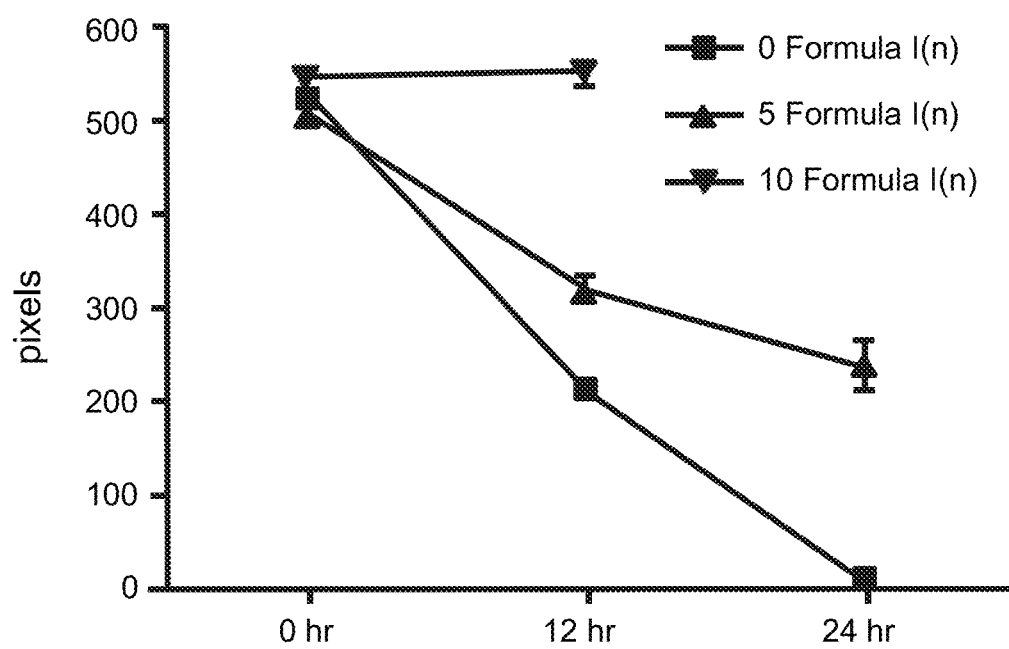
FIG. 3 is a graph of the distance between the migrating lips (as measured in pixels) vs. the time (hours) after administration of Formula I(n). Experiments were performed as described in FIG. 2.

By 24 hours, the control (0 µl Formula I(n)) cells have completely closed the in vitro wound (FIG. 2G and FIG. 3). In contrast, Formula I(n) treated cells showed reduced migration that for the higher Formula I(n) concentration was almost completely diminished (FIG. 2E, 2F, 2H and FIG. 3).

Example 8

Figure 4A:
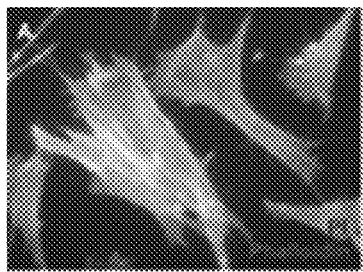
FIG. 4A is a micrograph of preconfluent neonatal foreskin fibroblast cells that have not been treated with Formula I(n). After 24 hours of mock treatment, cells were stained with phalloidin (actin-green) and propidium iodide (nuclei-red).
Figure 4D:
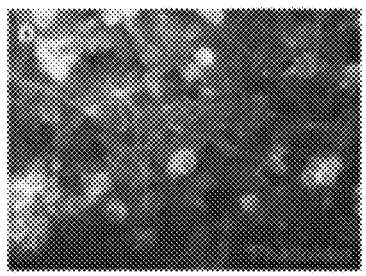
FIG. 4D is a micrograph of confluent MDA-MB231 breast cancer cells that have not been treated with Formula I(n). After 24 hours of mock treatment, cells were stained with phalloidin (actin-green) and propidium iodide (nuclei-red).
Figure 4G:
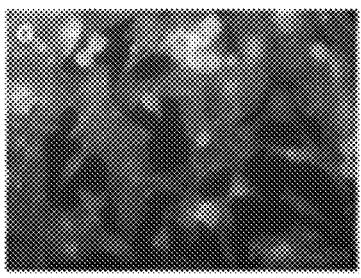
FIG. 4G is a micrograph of preconfluent MDA-MB231 breast cancer cells that have not been treated with Formula I(n). After 24 hours of mock treatment, cells were stained with phalloidin (actin-green) and propidium iodide (nuclei-red).
Figure 4B:
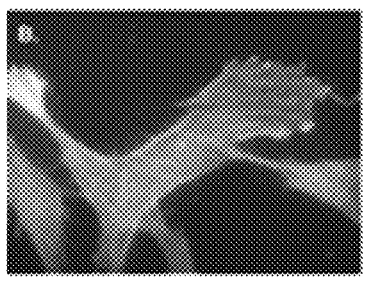
FIG. 4B is a micrograph of preconfluent neonatal foreskin fibroblast cells that have been treated with 5 µl/10 ml Formula I(n). After 24 hours of treatment, cells were stained with phalloidin (actin-green) and propidium iodide (nuclei-red).
Figure 4E:
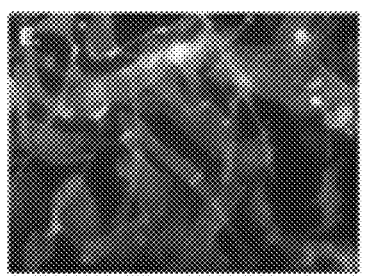
FIG. 4E is a micrograph of confluent MDA-MB231 breast cancer cells that have been treated with 5 µl/10 ml Formula I(n). After 24 hours of treatment, cells were stained with phalloidin (actin-green) and propidium iodide (nuclei-red).
Figure 4H:
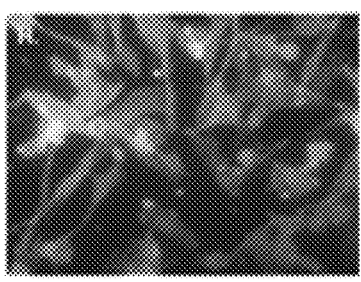
FIG. 4H is a micrograph of preconfluent MDA-MB231 breast cancer cells that have been treated with 5 µl/10 ml Formula I(n). After 24 hours of treatment, cells were stained with phalloidin (actin-green) and propidium iodide (nuclei-red).
Figure 4C:
FIG. 4C is a micrograph of preconfluent neonatal foreskin fibroblast cells that have been treated with 10 µl/10 ml Formula I(n). After 24 hours of treatment, cells were stained with phalloidin (actin-green) and propidium iodide (nuclei-red).
Figure 4F:
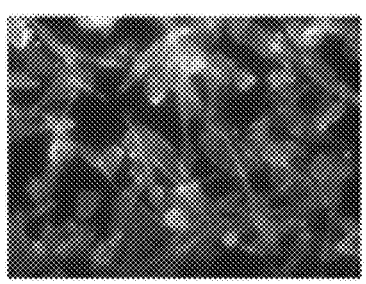
FIG. 4F is a micrograph of confluent MDA-MB231 breast cancer cells that have been treated with 10 µl/10 ml Formula I(n). After 24 hours of treatment, cells were stained with phalloidin (actin-green) and propidium iodide (nuclei-red).

Formula I(n) Induces Cytoskeletal Reorganization and Inhibits Tumor Cell Proliferation Formula I(n) was next analyzed for its ability to induce cytoskeletal reorganization. Fibroblasts were treated at preconfluent stages with 0 (FIG. 4A), 5 µl (FIG. 4B), or 10 µl (FIG. 4C) Formula I(n) for 24 hours and stained with phalloidin (actin-green) and propidium iodide (nuclei-red). Formula I(n) treated cells revealed a concentration dependent increase of staining intensity of the actin cytoskeleton, numerous filopodia and reduced staining at adhesion sites compared to controls consistent with reduced cell migration (See http://www.cellmigration.org/science/#overview for further discussion of cell migration).

Confluent MDA-MB231 breast cancer cells were treated with 0 (FIG. 4.D), 5 µl (E), or 10 µl (F) Formula I(n) for 24 hours and stained with phalloidin (actin-green) and propidium iodide (nuclei-red). Preconfluent MDA-MB231 breast cancer cells (FIG. 4) were treated with 0 (G), or 5 µl (H) µl Formula I(n) for 24 hours and stained with phalloidin (actin-green) and propidium iodide (nuclei-red).

As shown in FIG. 4, Formula I(n) treated tumor cells became elongated, spindle shaped, and consistent with their reduced ability to migrate, the actin filaments formed long parallel bundles in protrusions and spike-like thin sensory filopodia, but not broad lamellipodia that would be strong foundations for cell movement. In addition, at both Formula I(n) concentrations and at both stages of cell confluency, cell densities were significantly reduced upon treated with Formula I(n), thus reducing tumor cell proliferation.

Example 9

Reduced Focal Adhesion Kinase (FAK) [Tyr576] Phosphorylation in Formula I(n) Treated Cells It has previously been shown that reduced migratory ability of various invasive breast tumor cells, including MDA-MB231, Hs578T (Payne S L, Fogelgren B, Hess A R, Seftor E A, Fong S F T, Csiszar K, Hendrix M J C, and Kirschmann D A. Lysyl oxidase regulates breast cancer cell migration and adhesion through a hydrogen peroxide-mediated mechanism. Cancer Res. 65:11429-36, 2005), and astrocytoma cells (Laczko R, Szauter K M, Jansen M K, Hollosi P, Muranyi M, Molnar J, Fong K S K, Hinek A, Csiszar K. Active lysyl oxidase (LOX) correlates with FAK/paxillin activation and migration in invasive astrocytes. Neuropathol Appl Neurobiol. 33:631-43, 2007) was due to reduced activation of Focal Adhesion Kinase (FAK) and diminished SRC and/or Paxillin signaling. In order to determine the status of FAK activation in Formula I(n) treated cells, the phosphorylation status of FAK[Tyr576] in Hs578T cells treated with 5 and 10 µl Formula I(n) was analyzed.

In these experiments, Hs578T cells were cultured in standard DMEM, 1× Antibiotics and 10% FBS. Upon reaching confluency, cells were rinsed once with PBS and media changed to serum free, phenol red free DMEM. The cells were treated with 0, 5 or 10 µl Formula I(n)/10 ml media in 20 µl MeOH for 3 days. Protein from 6 days confluent conditioned cell culture media was collected and cell lysate samples were extracted using M-PER Mammalian Protein Extraction Reagent (Pierce, Rockford, Ill., USA) supplemented with Halt protease inhibitor (Pierce) and phosphatase inhibitors $Na_3VO_4$ (10 mM) and NaF (160 mM). Following cell lysis, protein concentration with Bradford reagent was determined using a Polarstar Optima microplate reader (BMG Labtechnologies, Durham, N.C., USA), and 20 µg protein was used for SDS-PAGE protein assay. The protein samples were size separated on 10% polyacrylamide gel and transferred onto PVDF membrane (Millipore, Billerica, Mass., USA) using semidry Bio-Rad (Hercules, Calif., USA) transfer system. Ponceau staining of the PVDF membranes was performed to ensure equal loading. The membranes were blocked with 5% non-fat dry milk in PBST overnight at 4° C. Membranes were washed in PBST, and rabbit anti-FAK [pTyr576] (1:1000, Biosource Inc., Camarillo, Calif., USA) antibody was applied on the membrane for 1 hour at room temperature. Membranes were then washed in PBST and incubated with anti-goat (Jackson Immuno Research, Baltimore, Pa., USA) horseradish peroxidase-conjugated secondary antibody for chemiluminescent detection. Subsequently, membranes were washed in PBS and incubated with ECL plus Western blotting reagent mix (Amersham Pharmacia Biotech).

Figure 5:
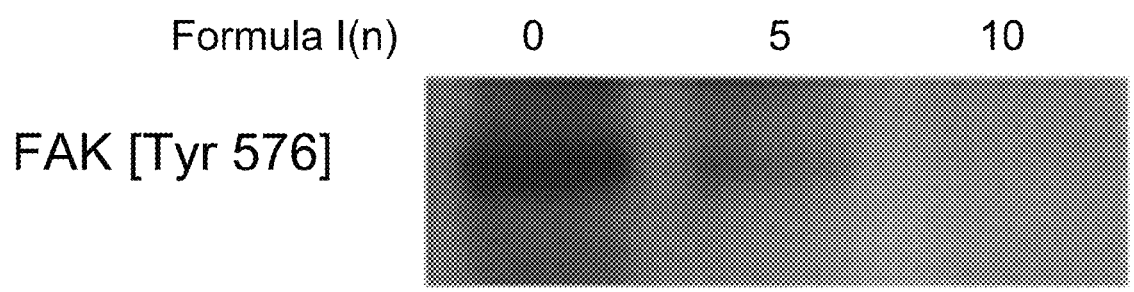
FIG. 5 is a western blot showing the inhibition of the phosphorylation of focal adhesion kinase (FAK) in Hs578T cells treated with Formula I(n). Antibodies that detect the FAK protein that has been phosphorylated on pTyr576 were used at a dilution of 1:1000 (rabbit anti-FAK[pTyr576] from Biosource Inc., Camarillo, Calif., USA). As described in Example 9, Formula I(n) induced a concentration dependent decrease of FAK[Tyr576] phosphorylation.

As shown in FIG. 5, Formula I(n) induced a concentration dependent decrease of FAK[Tyr576] phosphorylation.

Example 10

Efficacy of the Compounds in Breast Tumors In Vivo

A HER2-driven model of breast cancer (Muller W J, Sinn E, Pattengale P K, Wallace R, Leder P. Single-step induction of mammary adenocarcinoma in transgenic mice bearing the activated c-neu oncogene. Cell 1988; 54: 105-15), that expresses c-neu (the mouse ortholog of human HER2) driven by the MMTV promoter is used in the following example.

MMTV-neu mice are generated and observed post-lactation, with tumors observed with a median latency of approximately 25 weeks. Mice are enrolled in therapy studies when tumors reached a standard size (50-60 mm3) that permit easy serial assessment. Tumor-bearing mice are continuously treated with an active compound added to their chow. MMTV-c-neu mice are examined weekly to assess tumor development by palpation. Tumor volumes are calculated by the formula, Volume=$[(width)^2 \times length]/2$. Tumor-bearing mice are euthanized at the indicated times due to predefined morbidity, tumor ulceration, or a tumor size of more than 1.5 cm in diameter.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

The invention claimed is:

1. A method for the treatment of breast cancer in a host, comprising administering an effective amount of a compound of Formula III to a host in need thereof:

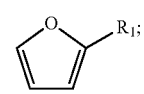

III wherein $R_1$ is an alkyl radical, an alkenyl radical, or an alkynyl radical having a carbon chain comprising $C_{10}$-$C_{22}$; and, wherein the compound of Formula III has a purity of greater than 98%.

2. The method of claim 1, wherein $R_1$ is an alkyl radical, an alkenyl radical, or an alkynyl radical having a carbon chain comprising $C_{12}$-$C_{20}$.

3. The method of claim 1, wherein $R_1$ is an alkyl radical, an alkenyl radical, or an alkynyl radical having a carbon chain comprising $C_{13}$-$C_{17}$.

4. The method of claim 1, wherein the compound is:

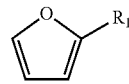

wherein;

$R_1$ is a $C_{12}$-$C_{20}$ alkyl chain comprising two or more double bonds.

5. The method of claim 1, wherein the compound is:

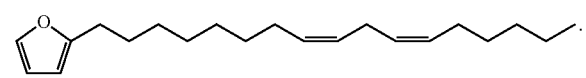 [SMILES: CCCCC/C=C\C/C=C\CCCCCCCc1ccco1]

6. The method of claim 1, wherein the breast cancer is an invasive breast cancer.

7. The method of claim 1, wherein the host is a human.

8. The method of claim 1, wherein the compound is administered in combination with a second therapeutic agent, wherein the second therapeutic agent is a chemotherapeutic agent.

9. The method of claim 1, wherein the compound is:

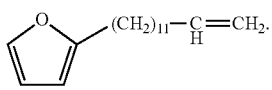

10. The method of claim 1, wherein the compound is:

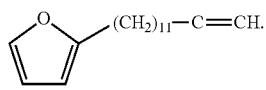

11. The method of claim 1, wherein the compound is

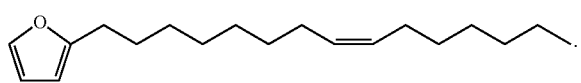

12. The method of claim 1, wherein the compound is

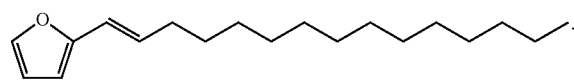 [SMILES: CCCCCCCCCCCCC/C=C/c1ccco1]

13. The method of claim 1, wherein the compound is

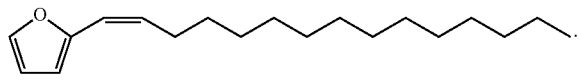 [SMILES: CCCCCCCCCCCCC/C=C\c1ccco1]

14. The method of claim 1, wherein the compound is

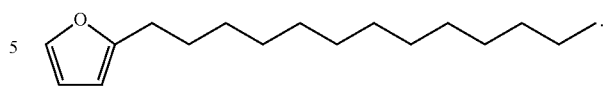

15. The method of claim 1, wherein the compound is

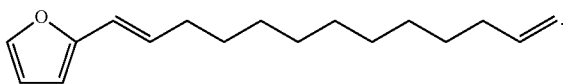 [SMILES: C=CCCCCCCCCC/C=C/c1ccco1]

16. The method of claim 1, wherein the compound is

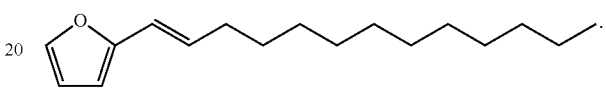

17. The method of claim 1, wherein the compound is

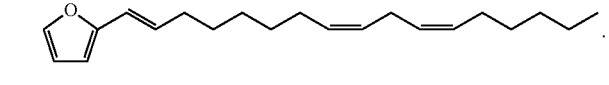 [SMILES: CCCCC/C=C\C/C=C\CCCCC/C=C/c1ccco1]

18. A method for the treatment of breast cancer in a host, comprising administering to a host in need thereof an effective amount of a compound of the formula

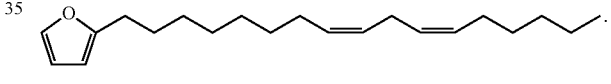

19. The method of claim 18, wherein the breast cancer is an invasive breast cancer.

20. The method of claim 18, wherein the host is a human.

21. The method of claim 18, wherein the compound is administered in combination with a second therapeutic agent, wherein the second therapeutic agent is a chemotherapeutic agent.

* * * * *